US010801073B2

(12) United States Patent
Bhowmick et al.

(10) Patent No.: US 10,801,073 B2
(45) Date of Patent: Oct. 13, 2020

(54) DEVICE, SYSTEM AND METHOD FOR CANCER PROGNOSIS AND USES THEREOF

(71) Applicant: Cedars-Sinai Medical Center, Los Angeles, CA (US)

(72) Inventors: Neil A. Bhowmick, Beverly Hills, CA (US); Diptiman Choudhury, Los Angeles, CA (US); Michael J. Baker, Portland, OR (US); Mark Sasha Drlik, Victoria (CA); Bjarne Hansen, Victoria (CA); Ayon Bhowmick, Beverly Hills, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 242 days.

(21) Appl. No.: 15/674,922

(22) Filed: Aug. 11, 2017

(65) Prior Publication Data
US 2017/0342506 A1 Nov. 30, 2017

Related U.S. Application Data

(63) Continuation of application No. PCT/US2016/017486, filed on Feb. 11, 2016.
(Continued)

(51) Int. Cl.
*C12Q 1/68* (2018.01)
*G01N 33/52* (2006.01)
(Continued)

(52) U.S. Cl.
CPC ......... *C12Q 1/6886* (2013.01); *C12Q 1/527* (2013.01); *G01N 33/52* (2013.01); *G01N 33/574* (2013.01);
(Continued)

(58) Field of Classification Search
CPC .............. C12Q 1/527; C12Q 1/6886; C12Q 2600/106; C12Q 2600/118; G01N 21/78; G01N 33/52; G01N 33/574; G01N 33/57484; G01N 2021/7763; G01N 2021/7786
(Continued)

(56) References Cited

U.S. PATENT DOCUMENTS

2007/0141605 A1 6/2007 Vann et al.
2012/0258472 A1 10/2012 Roy et al.
2014/0045193 A1 2/2014 Bhowmick et al.

FOREIGN PATENT DOCUMENTS

CA 2975895 A1 8/2016
WO 2014026157 A2 2/2014

OTHER PUBLICATIONS

Nygård et al., Plasma homocysteine levels and mortality in patients with coronary artery disease, N Engl J Med. Jul. 24, 1997;337(4):230-6.
(Continued)

*Primary Examiner* — Liban M Hassan
(74) *Attorney, Agent, or Firm* — Nixon Peabody LLP

(57) ABSTRACT

Modules, devices, systems and methods for measuring or detecting cysteine and/or methionine metabolite levels in a sample from a subject are disclosed. Various embodiments of the present invention concern modules, devices, systems and methods for prognosing or diagnosing cancer, for example, prostate, colon, ovarian or breast cancer; predicting the risk or probability of cancer recurrence; and/or for predicting, detecting and/or monitoring cystinuria or cystine stone disease.

20 Claims, 12 Drawing Sheets

Specification includes a Sequence Listing.

Related U.S. Application Data

(60) Provisional application No. 62/115,525, filed on Feb. 12, 2015.

(51) Int. Cl.
    *G01N 33/574*     (2006.01)
    *C12Q 1/6886*     (2018.01)
    *C12Q 1/527*     (2006.01)
    *G01N 21/77*     (2006.01)
    *G01N 21/78*     (2006.01)

(52) U.S. Cl.
    CPC .. *G01N 33/57484* (2013.01); *C12Q 2600/106* (2013.01); *C12Q 2600/118* (2013.01); *G01N 21/78* (2013.01); *G01N 2021/7763* (2013.01); *G01N 2021/7786* (2013.01)

(58) Field of Classification Search
    USPC .......................................... 435/288.7, 289.1
    See application file for complete search history.

(56) References Cited

OTHER PUBLICATIONS

Nishiuch et al., Cytotoxicity of cysteine in culture media, In Vitro. Sep. 1976;12(9):635-8).

Dudman et al., Human arterial endothelial cell detachment in vitro: its promotion by homocysteine and cysteine, Atherosclerosis. Nov. 1991;91(1-2):77-83.

Jacob et al., Cysteine is a cardiovascular risk factor in hyperlipidemic patients, Atherosclerosis. Sep. 1999;146(1):53-9.

Araki et al., Plasma sulfhydryl-containing amino acids in patients with cerebral infarction and in hypertensive subjects, Atherosclerosis. Oct. 1989;79(2-3):139-46.

Mansoor et al., Redox status and protein binding of plasma homocysteine and other aminothiols in patients with early-onset peripheral vascular disease. Homocysteine and peripheral vascular disease, Arterioscler Thromb Vasc Biol. Feb. 1995;15(2):232-40.

Mills et al., Blood glutathione and cysteine changes in cardiovascular disease, J Lab Clin Med. May 2000;135(5):396-401.

Guerra et al. (Cystinuria: description of a simple method of determination and our 5-year clinical experience, Acta Biomed Ateneo Parmense. 1990;61(1-2):85-90.

El-Brashy et al. (Colorimetric determination of some amino acids containing a sulfur group, Pharm World Sci. Mar. 24, 1995;17(2):54-7.

Schneider et al. (Colorimetric assay of cystine using noradrenochrome, Anal. Biochem., Apr. 1968, 23(1):129-131.

Yuan et al., Glutathione-protected silver nanoclusters as cysteine-selective fluorometric and colorimetric probe, Anal Chem. Feb. 5, 2013;85(3):1913-9.

ISR-WO PCT/US2016/017486 dated May 2, 2016, 13 pages.

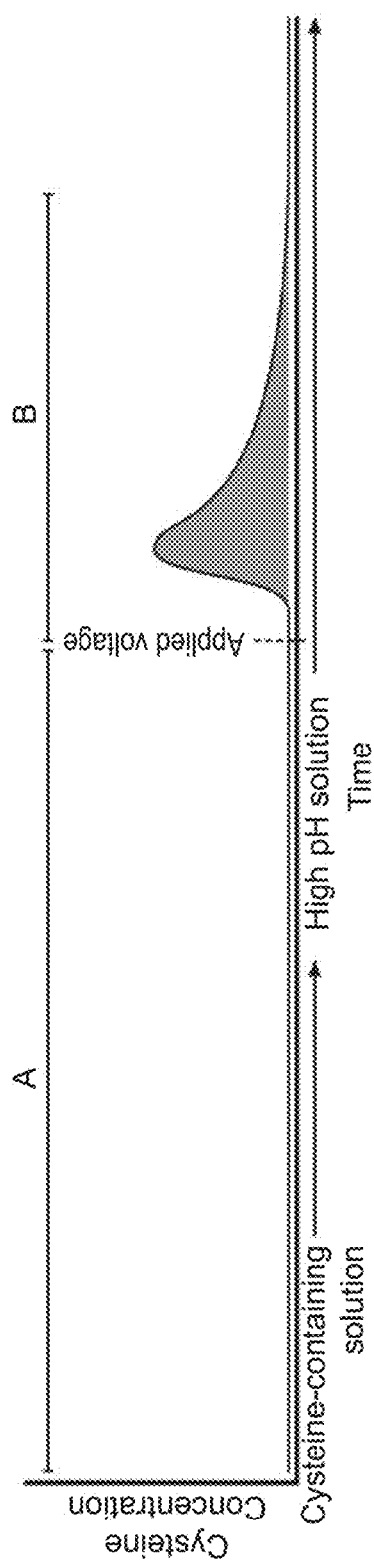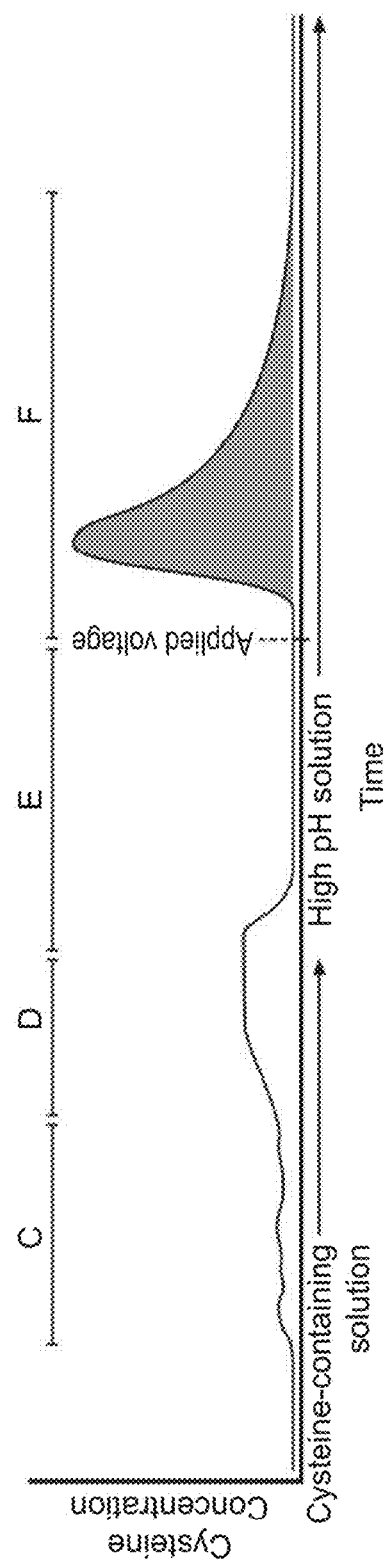

DEVICE, SYSTEM AND METHOD FOR CANCER PROGNOSIS AND USES THEREOF

CROSS REFERENCE TO RELATED APPLICATION

This application is a continuation application of International Application No. PCT/US2016/017486, filed on Feb. 11, 2016, which was published in English under PCT Article 21(2), which in turn claims priority under 35 U.S.C. § 119(e) to U.S. provisional patent application No. 62/115,525, filed on Feb. 12, 2015. These prior applications are incorporated herein by reference.

FIELD

This invention relates to oncology, urology and cardiology. More specifically, this invention relates to devices, systems and methods for predicting the risk or probability of cancer recurrence in a subject before, during, or after cancer treatment; and devices, systems and methods for detecting a methionine metabolite in a sample from a subject. Also, this invention relates to devices, systems and methods for diagnosing and monitoring circulating cysteine levels for individuals with heart or cardiovascular disease and urinary tract cystine stone disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Prostate cancer remains the most common non-cutaneous solid malignancy in the United States, and the second leading cause of cancer specific death in men. Nevertheless, it has become increasingly clear that not all men who are diagnosed with prostate cancer require intervention. Yet, many men that receive surgical or radiation-based primary treatment develop recurrent disease. Prior to surgical intervention, serum PSA, biopsy Gleason grade, and clinical stage help determine if patients are likely to be recurrent versus those that may remain localized and possibly remain clinically inconsequential. Various approaches in improving the role of PSA in early prostate cancer detection have been tested, but their benefit to overall survival is yet to be proven. Ultimately, there is a subgroup of men without conventional negative factors harboring high risk, aggressive disease and are even at elevated risk of early recurrence after attempted definitive local therapy. Also, for diagnosing breast cancer, the distinguishing of those that may progress is critical to maintaining good quality of life. The ongoing challenge facing clinicians is how to identify the cohort of cancer patients at high risk, from the larger cohort of cancer patients who are likely harboring more indolent disease.

Cystinuria, is a common genetic metabolic disorder (1 in 7000), accounting for 1-2% of all cases of renal lithiasis. Cystine crystals are a result of precipitate in the kidney and accumulation in the bladder to form calculi with a diameter of up to 5 mm. Cystine is a result of the oxidation of two cysteine molecules that covalently link via a disulfide bond. Impaired reabsorption of cystine leads to a high risk for the formation of cystine calculi in the urinary tract, potentially causing obstruction, infections and eventually renal failure. Patients with cystinuria can control circulating cysteine through dietary modifications and increased fluid intake. Such patients are often treated with cystine solubilizing drugs like D-penicillamine, mercaptopropionylglycine or Captopril. Frequently, interventions like lithotripsy are required. Urinary tract obstruction can lead to hydronephrosis and ultimately to loss of renal function. The ready detection of cysteine in urine and blood of such individuals by a point of care device can enable self-dietary modification and indicate clinical intervention at an early stage to prevent renal damage and loss of function.

Myocardial infarction (MI) (i.e., heart attack) is the irreversible damage of heart muscle secondary to prolonged ischemia. Approximately 1.5 million cases of MI occur annually in the United States. Plasma homocysteine is an established independent risk factor for MI and coronary artery disease (Nygård et al., *Plasma homocysteine levels and mortality in patients with coronary artery disease*, N Engl J Med. 1997 Jul 24; 337(4):230-6). However, as circulating cysteine is a biologic marker for oxidative stress, its application in heart, coronary artery, and peripheral vascular disease after an MI is a point of significant study. Cysteine has a general cytotoxicity in vitro (Nishiuch et al., *Cytotoxicity of cysteine in culture media*, In Vitro. 1976 September; 12(9):635-8) and promotes detachment of human arterial endothelial cells in culture (Dudman et al., *Human arterial endothelial cell detachment in vitro: its promotion by homocysteine and cysteine*, Atherosclerosis. 1991 November; 91(1-2):77-83). A cohort study (where blood pressure, smoking status, total cholesterol, LDL-cholesterol and triglycerides did not statistically differ between groups) cysteine levels were higher in patients with cardiovascular disease than in asymptomatic patients, respectively $254.7 \pm 47.7$ versus $239.1 \pm 44.3$ µmol/l (P=0.003) (Jacob et al., *Cysteine is a cardiovascular risk factor in hyperlipidemic patients*, Atherosclerosis. 1999 September; 146(1):53-9). Age adjusted cysteine levels differed significantly between groups (P=0.027) while the P-value was of borderline significance for homocysteine (P=0.09). These data suggested that plasma total cysteine is a risk factor for atherosclerosis in hyperlipidemic patients. Multiple other studies have shown a relationship between total cysteine and vascular occlusive disease (Araki et al., *Plasma sulfhydryl-containing amino acids in patients with cerebral infarction and in hypertensive subjects*, Atherosclerosis. 1989 October; 79(2-3):139-46; Mansoor et al., *Redox status and protein binding of plasma homocysteine and other aminothiols in patients with early-onset peripheral vascular disease. Homocysteine and peripheral vascular disease*, Arterioscler Thromb Vasc Biol. 1995 February; 15(2):232-40; Mills et al., *Blood glutathione and cysteine changes in cardiovascular disease*, J Lab Clin Med. 2000 May; 135(5):396-401). In these studies, significantly higher cysteine concentrations were found in afflicted patients than controls.

As such, for an informed clinical decision, there still exists a great need for devices, systems and methods that can predict the risk or probability of recurrent cancer, and that can predict, diagnose, prognosticate, and/or monitor cancer, aggressive cancer, recurrent cancer, cardiovascular disease, and cystinuria and urinary tract cystine stone disease.

SUMMARY

Disclosed embodiments provide a device, system and method that address the needs discussed above. Certain disclosed embodiments concern a system comprising an enzyme reaction module that includes an enzyme reaction chamber having at least one inlet and at least one outlet. The enzyme reaction chamber is configured to conduct a fluid flow from the inlet, through the enzyme reaction chamber, to the outlet. The system also includes a sequestration-liberation module comprising a sequestration-liberation chamber having gold particles located therein and comprising at least one inlet and at least one outlet. The sequestration-liberation chamber is configured to conduct a fluid flow from the inlet, through the sequestration-liberation chamber, to the outlet. Electrodes are configured to conduct an electric current through the gold particles. The electrodes apply a suitable voltage, which for certain disclosed embodiments is from about 1 to about 10 volts. The system also includes a detection module comprising a detection channel comprising at least one inlet and at least one outlet. The detection channel is located between the first and second apertures and is configured to conduct a fluid flow from the inlet, through the detection channel, to the outlet. The first and second apertures are configured to conduct a light beam from the first aperture, across the detection channel, to the second aperture. The system is configured to conduct a fluid flow from the enzyme reaction module, through the sequestration-liberation module, and to the detection module. The system may further comprise or be supplied with cystathionine synthase, cystathionine lyase, wash or exchange buffer, and detection reagent. A biological sample obtained from a subject is supplied to the system. In certain embodiments, the cystathionine synthase and/or cystathionine lyase is immobilized on a solid support.

The enzyme reaction chamber may be shaped as a column and certain disclosed embodiments have a length of about 1-1000 mm and a diameter of about 0.1-100 mm. The sequestration-liberation chamber also may be shaped as a column, with certain disclosed embodiments having a length of about 1-1000 mm and/or a diameter of about 0.1-100 mm. The enzyme reaction module may further comprise a filter located before the enzyme reaction chamber and along a fluid flow pathway for filtering a biological sample, enzyme, reagent, buffer, fluid flow, and/or reaction mixture.

The system may further comprise a buffer cartridge configured to hold a wash or exchange buffer. The buffer cartridge supplies wash or exchange buffer to at least one inlet of the sequestration-liberation chamber. For certain embodiments, the exchange buffer has a pH of about 8-14.

For certain embodiments, the detection channel has a width of about 0.1-1000 mm. At least one inlet of the detection channel is configured to receive a detection reagent.

The detection module may further comprise a third aperture and an optical filter located between the second and third apertures. The second and third apertures are configured to conduct a light beam from the second aperture, across the optical filter, which filters the light beam, to the third aperture. The detection module may further comprise a light source configured to emit a light beam into the first aperture. A photosensor is configured to detect the light beam transmitted out of the third aperture. The photosensor may be configured to generate a current or voltage output from detected transmission light.

The system may further comprise a spectrometer. The spectrometer is configured to emit a light beam into the first aperture and to detect transmission light intensity out of the third aperture.

A particular disclosed embodiment of the system comprises an enzyme reaction module comprising an enzyme reaction chamber comprising at least one inlet and at least one outlet. The enzyme reaction chamber is configured to conduct a fluid flow from the inlet, through the enzyme reaction chamber, to the outlet. The system also comprises a sequestration-liberation module comprising a sequestration-liberation chamber having gold particles located therein and comprising at least one inlet and at least one outlet. The sequestration-liberation chamber is configured to conduct a fluid flow from the inlet, through the sequestration-liberation chamber, to the outlet. Electrodes are configured to conduct an electric current through the gold particles. The system also includes a detection module comprising a detection channel comprising at least one inlet and at least one outlet. The detection channel is configured to conduct a fluid flow from the inlet, through the detection channel, to the outlet. The system also comprises a first aperture, a second aperture, a third aperture, and an optical filter. The detection channel is located between the first aperture and the second aperture, and the optical filter is located between the second aperture and the third aperture. The three apertures and the optical filter are configured to conduct a light beam from the first aperture, across the detection channel, to the second aperture, across the optical filter, and to the third aperture. A light source is configured to emit a light beam into the first aperture. A photosensor is configured to detect the light beam transmitted out of the third aperture and to generate a current or voltage output from the detected transmission light. The light source may be a spectrometer configured to emit a light beam into the first aperture and to detect the transmission light intensity out of the third aperture. The system is configured to conduct a fluid flow from the enzyme reaction module, through the sequestration-liberation module, and to the detection module.

A method for using the system also is disclosed. The system may include, or is supplied with, cystathionine synthase, cystathionine lyase, wash or exchange buffer, and detection reagent. A biological sample is obtained from a subject, and the sample is supplied to the system. The system is operated to generate an output, such as a generated current or voltage output that may be used to calculate a cysteine and/or methionine metabolite level in the biological sample. The method may further comprise diagnosing or prognosticating a cancer based on the detected cysteine and/or methionine metabolite level.

A particular disclosed method embodiment comprises providing a disclosed system that includes or is supplied with cystathionine synthase, cystathionine lyase, wash or exchange buffer, and detection reagent. A biological sample obtained from a subject is supplied to the system. The system is operated, and a transmission light intensity is detected out of the third aperture. The detected transmission light intensity is used to calculate a cysteine and/or methionine metabolite level in the biological sample. The method may further comprise diagnosing or prognosticating a cancer based on the detected cysteine and/or methionine metabolite level.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 5 depicts, in accordance with various embodiments of the present invention, a cysteine concentration curve.

FIG. 6 depicts, in accordance with various embodiments of the present invention, a cysteine concentration curve showing scenarios that may occur.

DETAILED DESCRIPTION

Figure 1A:
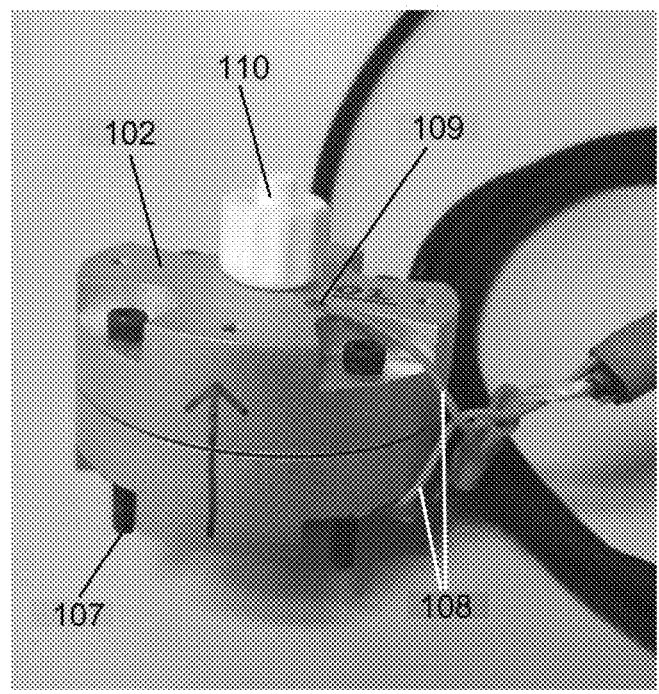
FIGS. 1A-1B depict, in accordance with various embodiments of the present invention, that one non-limiting example of the cysteine sequestration/liberation module as described herein comprises a gold cartridge assembly.

All references cited herein are incorporated by reference in their entirety as though fully set forth. Unless defined otherwise, technical and scientific terms used herein have the same meaning as commonly understood by one of ordinary skill in the art to which this invention belongs. Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013) provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

The term "sample" or "biological sample" as used herein denotes a sample taken or isolated from a biological organism, e.g., a blood or urine sample from a subject. Exemplary biological samples include, but are not limited to, whole blood, blood, processed blood, lysed blood, serum; plasma; urine; saliva; semen; lymph; and other body fluid or biofluid etc. The term also includes a mixture of the above-mentioned samples. The term "sample" also includes untreated or pretreated (or pre-processed) or treated (processed) biological samples. As one non-limiting example, a blood sample can be processed with an anticoagulant such as coumarins (vitamin K antagonists), warfarin (Coumadin). acenocoumarol, phenprocoumon, atromentin, brodifacoum, phenindione, heparin and heparin derivatives, low molecular weight heparin, synthetic pentasaccharide inhibitors of factor Xa, fondaparinux, idraparinux, direct factor Xa inhibitors, rivaroxaban, apixaban, edoxaban, betrixaban, darexaban, letaxaban, eribaxaban, direct thrombin inhibitors, hirudin, lepirudin, bivalirudin, argatroban, dabigatran, ximelagatran, antithrombin protein therapeutics, Atryn, batroxobin, hementin, Ethylene Diamine Tetra Acetic Acid (EDTA), citrate, sodium citrate, acid-citrate-dextrose, and oxalate. As another non-limiting example, a blood sample can be lysed, that is, red blood cells can be lysed using various lysis buffers (e.g., ACK lysing buffer and isotonic NH4Cl solution). As still another non-limiting sample, a blood sample can be pelleted in a low-speed centrifugation step.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., prostate, colon, ovarian or breast cancer, cardiovascular disease, cystinuria and cystine stone disease) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

As used herein, "a variant" or "a mutant" can include, but are not limited to, SNP variant, splicing variant, degenerate variant, biologically active portion of a nucleic acid or polypeptide, a nucleic acid or polypeptide having conservative amino acid mutation, deletion, insertion, fusion, or any mutation as compared to a wild type or reference sequence, and a combination thereof. A "degenerate variant" as used herein refers to a variant that has a mutated nucleotide sequence, but still encodes the same polypeptide due to the redundancy of the genetic code. In accordance with the present invention, the enzyme protein can be modified, for example, to facilitate or improve identification, expression, isolation, storage and/or administration, so long as such modifications do not reduce the enzyme's function to unacceptable level. In various embodiments, a variant of the enzyme protein has at least 10%, 20%, 30%, 40%, 50%, 60%, 70%, 80%, 90%, or 95% of the function of a wild-type enzyme protein. Examples of the enzyme include but are not limited to cystathionine beta-synthase and cystathionine gamma-lyase.

The term "functional" when used in conjunction with "equivalent", "analog", "derivative", "variant", "mutant", or "fragment" refers to an entity or molecule which possess a biological activity that is substantially similar to a biological activity of the entity or molecule of which it is an equivalent, analog, derivative, variant, mutant or fragment thereof.

Systems

Various embodiments of the present invention provide for a system that comprises one or more of the following components, modules and devices: biological sample; sample collector; sample reservoir or cartridge; filtration module; enzyme reaction module; enzyme; enzyme reservoir or cartridge, sequestration-liberation module, buffer, buffer reservoir or cartridge, power supply; electric wires and switches, detection module; spectrometer; detection reagent, detection reagent reservoir or cartridge; pump; vacuum, fluid channels or tubes; control module; and data storage and analysis module.

Various embodiments of the present invention provide a system comprising: an enzyme reaction module, a sequestration-liberation module, and a detection module. In various embodiments, the system is configured to conduct a fluid flow from the enzyme reaction module, through the sequestration-liberation module, to the detection module.

In some embodiment, the system further comprises a biological sample obtained from a subject. In some embodiment, the system further comprises a cystathionine synthase and/or a cystathionine lyase. In one embodiment, the cystathionine synthase is a cystathionine beta-synthase and/or the cystathionine lyase is a cystathionine gamma-lyase. In some embodiment, the system further comprises a wash or exchange buffer. In some embodiment, the system further comprises a detection reagent.

In various embodiments, a system described herein further comprises a filtration module configured to filter the fluid flow into the enzyme reaction module, the sequestration-liberation module, and/or the detection module. In various embodiments, a system described herein further comprises a pump and/or vacuum configured to drive the liquid flow through the system. In various embodiments, a system described herein further comprises one or more pressure gauges or sensors configured to monitor the pressure at one or more locations inside the system.

In various embodiments, a biological sample is obtained from a subject. In some embodiments, the biological sample is obtained using a sample collector as described herein. In various embodiments, the biological sample is filtered using a filtration module as described herein. In some embodiments, the biological sample is stored in a sample reservoir or cartridge as described herein before being transferred into an enzyme reaction module as described herein. In other embodiments, the biological sample is directly transferred into an enzyme reaction module as described herein.

In various embodiments, the biological sample is transferred into an enzyme reaction module as described herein. In some embodiments, the biological sample is filtered using a filtration module as described herein before being transferred into the enzyme reaction module. In some embodiments, the enzyme reaction module contains enzymes as described herein, and the enzymes process the biological sample. In other embodiments, an enzyme reservoir or cartridge as described herein is connected to the enzyme reaction module, and the enzymes contained therein are transferred into the enzyme reaction module so as to process the biological sample. In some embodiments, the enzyme reaction module contains buffers for the enzymatic reaction. In other embodiments, buffer reservoirs or cartridges as described herein are connected to the enzyme reaction module, and the buffers contained therein are transferred into the enzyme reaction module for the enzymatic reaction. In various embodiments, the biological sample, enzymes, and buffers can be transferred simultaneously or sequentially in any suitable order.

In various embodiments, the processed biological sample is transferred into a sequestration-liberation module as described herein. In some embodiments, the biological sample is filtered using a filtration module as described herein before being transferred into the sequestration-liberation module. In some embodiments, the sequestration-liberation module contains gold particles and electrodes as described herein. In various embodiments, the gold particles first sequester cysteine in the biological sample, and then the electrodes conduct an electric current through the gold particles to liberate the sequestered cysteine. In some embodiments, the sequestration-liberation module contains buffers for the sequestration, washing and/or liberation steps. In other embodiments, buffer reservoirs or cartridges as described herein are connected to the sequestration-liberation module, and the buffers contained therein are transferred into the sequestration-liberation module for the sequestration, washing and/or liberation steps. In various embodiments, the biological sample and buffers can be transferred simultaneously or sequentially in any suitable order.

In various embodiments, the liberated cysteine is transferred into a detection module as described herein. In some embodiments, the detection module contains a detection reagent as described herein, and the detection reagent reacts with the liberated cysteine. In other embodiments, a detection reagent reservoir or cartridge as described herein is connected to the detection module, and the detection reagent contained therein is transferred into the detection module so as to react with the liberated cysteine. In some embodiments, the detection module contains buffers for the detection reaction. In other embodiments, buffer reservoirs or cartridges as described herein are connected to the detection module, and the buffers contained therein are transferred into the detection module for the detection reaction. In various embodiments, the biological sample, detection reagent, and buffers can be transferred simultaneously or sequentially in any suitable order.

In some embodiments, the reaction between the detection reagent and the liberated cysteine creates new molecules, complexes and structures that are fluorescent or colorimetric, or have changes in absorption spectrum and/or emission spectrum, and a spectrometer as described herein detects such fluorescent/colorimetric molecules, complexes and structures, or detects such changes in absorption spectrum and/or emission spectrum. In some embodiments, the spectrometer is part of the detection module. In other embodiments, the spectrometer is a separate component from the detection module.

In various embodiments, the detection modules or the spectrometer outputs a signal to a data storage and analysis module as described herein. In various embodiments, the data storage and analysis module stores the output signal and analyzes the output signal to calculate the cysteine level in the biological sample for various applications as described herein.

In various embodiments, a power supply as described herein is used to provide electricity necessary for the system and its components, for example, the sequestration-liberation module, the detection module, and the data storage and analysis module. In various embodiments, a pump and/or vacuum as described herein is used to drive the liquid flow through the system and its components. In various embodiments, one or more pressure gauges or sensors as described herein are used to monitor the pressure at one or more locations inside the system. In various embodiments, a control module (for example, a computer) is used to control the system and its components. In various embodiments, electric wires and switches, fluid channels or tubes, and other suitable parts are used to connect the components of the system.

In various embodiments, one or more components of a system described herein are miniaturized to minimize the sample size required from a subject. In some embodiments, the sample volume is about 1-2, 2-5, 5-10, 10-20, 20-50, 50-100, 100-200, 200-500, 500-1000, or 1000-2000 µL.

In various embodiments, the components of a system described herein are provided as separate items, which can be connected through electric wires and fluid tubes.

In various embodiments, the components of a system described herein are provided as one integral part or unit.

In some embodiments, the components of a system described herein are provided as two or more integral parts or units. For example, a first integral part or unit is a machine comprising power supply, electric wires and switches, spectrometer, pump, vacuum, fluid channels or tubes, control module, and/or data storage and analysis module; a second integral part or unit is a single use or disposable processing cartridge comprising the filtration, enzyme reaction, sequestration-liberation, and/or detection modules; a third integral part or unit comprises the sample cartridge; and other integral parts or units comprise one or more of enzyme cartridge, buffer cartridge, and detection reagent cartridge. A user can plug or install the disposable processing cartridge, sample cartridge, enzyme cartridge, buffer cartridge, and detection reagent cartridge into the machine, and can then operate the machine to carry out the whole process, as the machine moves the biological sample, enzymes, buffers and detection reagents through the system, detects a cysteine level in the biological sample, and makes a prostate, colon, ovarian or breast cancer diagnosis for the subject. After use, the user only needs to replace the disposable processing cartridge and sample cartridge, and when necessary, to replace the enzyme cartridge, buffer cartridge, and detection reagent cartridge. In some embodiments, the machine automates the whole process and requires little or no manual operation from the user. In other embodiments, the machine needs additional manual operation from the user and hence the user can have more control of the whole process.

As a non-limiting example of the work flow, the user uses a sample collector to collects a biological sample (e.g., blood or urine) from a subject. The biological sample may be directly stored into a sample cartridge, or may be first filtered then stored in the sample cartridge. The user then inserts the sample cartridge into a machine which includes power supply, electric wires and switches, pump, vacuum, fluid channels or tubes, spectrometer, control module, and data storage and analysis module. Also, the user inserts into the machine various other parts, for example, filtration module, enzyme reaction module, enzyme cartridge, sequestration-liberation module, detection module, detection reagent cartridge, and buffer cartridges. Alternatively, one or more of these parts have been previously placed in to the machine. These parts may be provided as separate items; or as one or more integrated items for convenience. Alternatively, some of these parts may be integrated into the machine, for example, the enzyme, detection reagent and buffer cartridges, as they can be filled with sufficient contents for processing multiple samples. Once the machine contains the needed modules and/or components, the user actives the machine to start the process. The machine passes the biological sample from the sample cartridge through the filtration module into the enzyme reaction module. The machine also passes enzymes and enzyme buffer into the enzyme reaction module to process biological sample enzymatically. The machine then passes the processed sample into the sequestration-liberation module to allow gold particles contained therein to sequester cysteine from the processed sample. After the processed sample passes the sequestration-liberation module, washing buffer is passed through the sequestration-liberation module to wash the gold particles. The machine applies an electric current through the gold particles, liberates the sequestered cysteine, and passes the liberated cysteine into the detection module. The machine also passes the detection reagent and detection buffer into the detection module to react with the liberated cysteine. The reaction generates fluorescent/colorimetric targets and/or results in changes in absorption spectrum and/or emission spectrum, and such fluorescent/colorimetric targets and/or changes in absorption spectrum and/or emission spectrum are detected by the spectrometer to generate a signal data. The signal data is transferred to the data storage and analysis module. The data storage and analysis module further analyzes the signal data to calculate the cysteine level in the biological sample and to determine disease diagnosis and prognosis as described herein.

In various embodiments, a system described herein is provided as a point-of-care (POC) device that detects cysteine, cystathionine and/or homocysteine in a single test in a self-contained system. Detection of cysteine, cystathionine and/or homocysteine can be used as a prognostic test for prostate, colon, ovarian or breast cancer, or can be used to predict, diagnose, prognosticate, and/or monitor cystinuria, cystine stone disease, or cardiovascular disease. The device can analyze cysteine, cystathionine and/or homocysteine in blood, serum and urine samples. The device improves on the current laboratory based method by allowing a user to quantify cysteine, cystathionine and/or homocysteine in a single device. In another embodiment, the device quantifies cysteine, cystathionine and/or homocysteine using polymer coated gold nanorods or carbon nanorods having gold-coated tips. In yet another embodiment, the device quantifies cysteine, cystathionine and/or homocysteine using colorimetric and/or fluorescent detection assays and reagents. In still another embodiment, the device employs electrochemical detection of cysteine, cystathionine and/or homocysteine, where an optical component to detect cysteine, cystathionine and/or homocysteine in the sample may not be necessary. In various embodiments, cystathionine and/or homocysteine can be enzymatically converted into cysteine to provide enhanced prognostic value associated with methionine metabolites. In various embodiments, the device contains gold particles (e.g. nanoparticles, microspheres) or gold plates or foils for detecting levels of cysteine, cystathionine and/or homocysteine in a biological sample, such as whole blood, serum, plasma, and/or urine.

Biological Samples

In various embodiments, the system comprises a biological sample isolated from a subject. In some embodiments, the biological sample is urine. In some embodiments, the biological sample is whole blood, blood, processed blood, lysed blood, serum, or plasma. In one embodiment, the biological sample is a blood sample treated with an anticoagulant. In another embodiment, the biological sample is a blood sample in which red blood cells and/or other cells are lysed. Still in another embodiment, the biological sample is a blood sample in which red blood cells and/or other cells are pelleted and removed. In one embodiment, the biological sample is a finger prick volume of blood. In one embodiment, as serum contains particles larger than the target cysteine, an about 3 kDa MW cut off spin filter is utilized to filter the serum sample to reduce interferences.

In various embodiments, the sample volume is about 1-2, 2-5, 5-10, 10-20, 20-50, 50-100, 100-200, 200-500, 500-1000, or 1000-2000 µL. In certain embodiments, the flow rate of the sample through the various components of a system described herein is about 1-2, 2-5, 5-10, 10-20, 20-50, 50-100, 100-200, or 200-500 µL/min, or a combination thereof. In some embodiments, the flow rate of the sample is substantially the same in the various components. In some embodiments, the flow rate of the sample is different in the various components. In some embodiments, a pump or vacuum is used to push or pull the fluid flow through the system, and hence is used to control the flow rate through various components and modules.

Sample Collector, Reservoir or Cartridge

In various embodiments, the system comprises a sample collector. Various embodiments of the present invention provide for a sample collector. In various embodiments, the sample collector is connected to an enzyme reaction module described herein and transfers the sample into the enzyme reaction module. In certain embodiments, a filtration module is placed between the sample collector and the enzyme reaction module.

Figure 12:
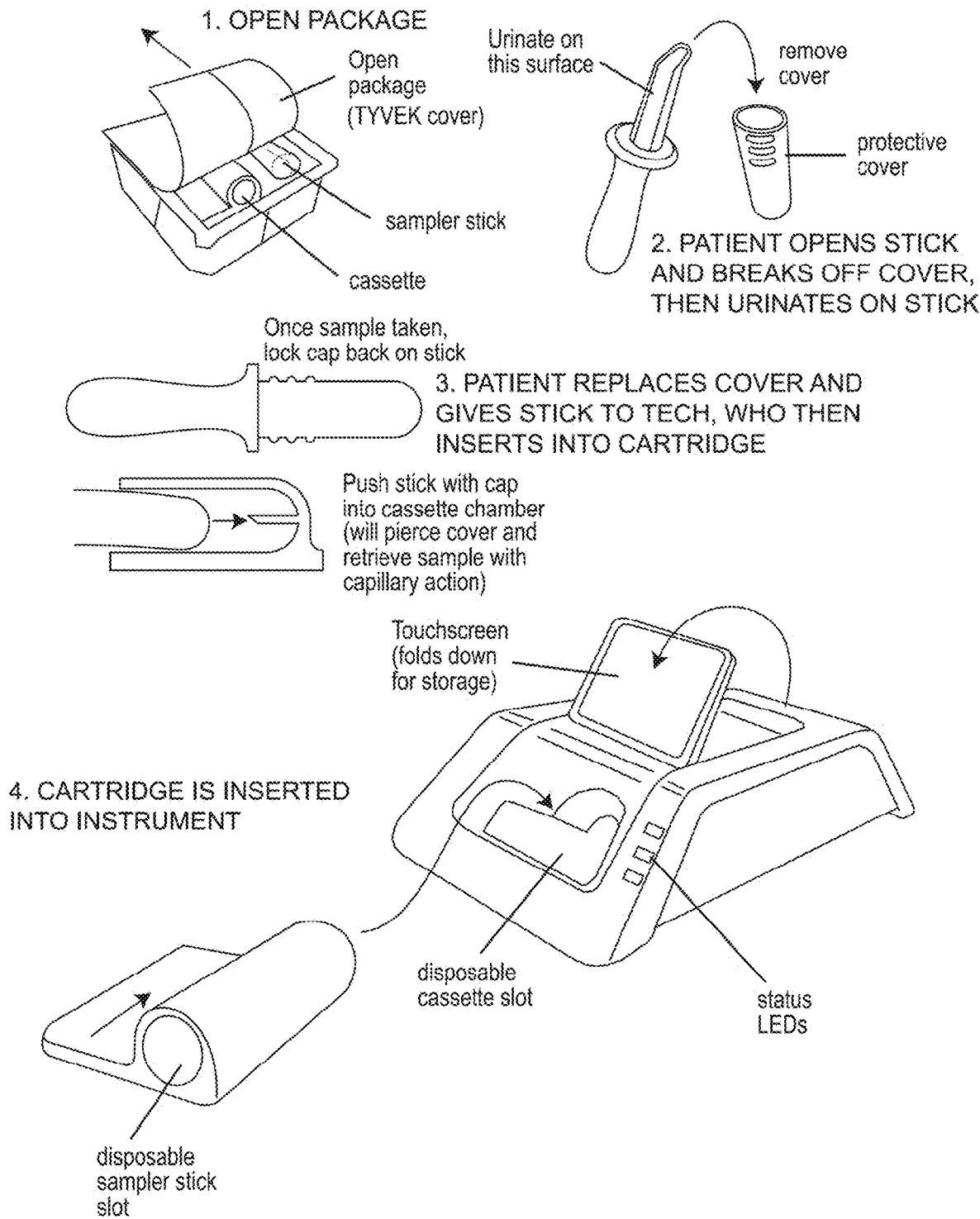
FIG. 12 depicts, in accordance with various embodiments of the present invention, one non-limiting example of a system described herein. This non-liming example applies a urine test.

In some embodiments, the sample collector is configured to collect a urine sample from the subject. For example, the urine sample collector can comprise a stick comprising a rigid structure configured for holding and an absorbent composition to collect the urine. The urine sample collector is configured for a subject to urinate on the absorbent composition or for the subject to dip the absorbent end into a container comprising the urine sample. The urine sample collector can further comprise a cover that is removably attached to the rigid structure. FIG. 12 illustrates one non-limiting example of a system described herein that comprises a urine sample collector.

Figure 13:
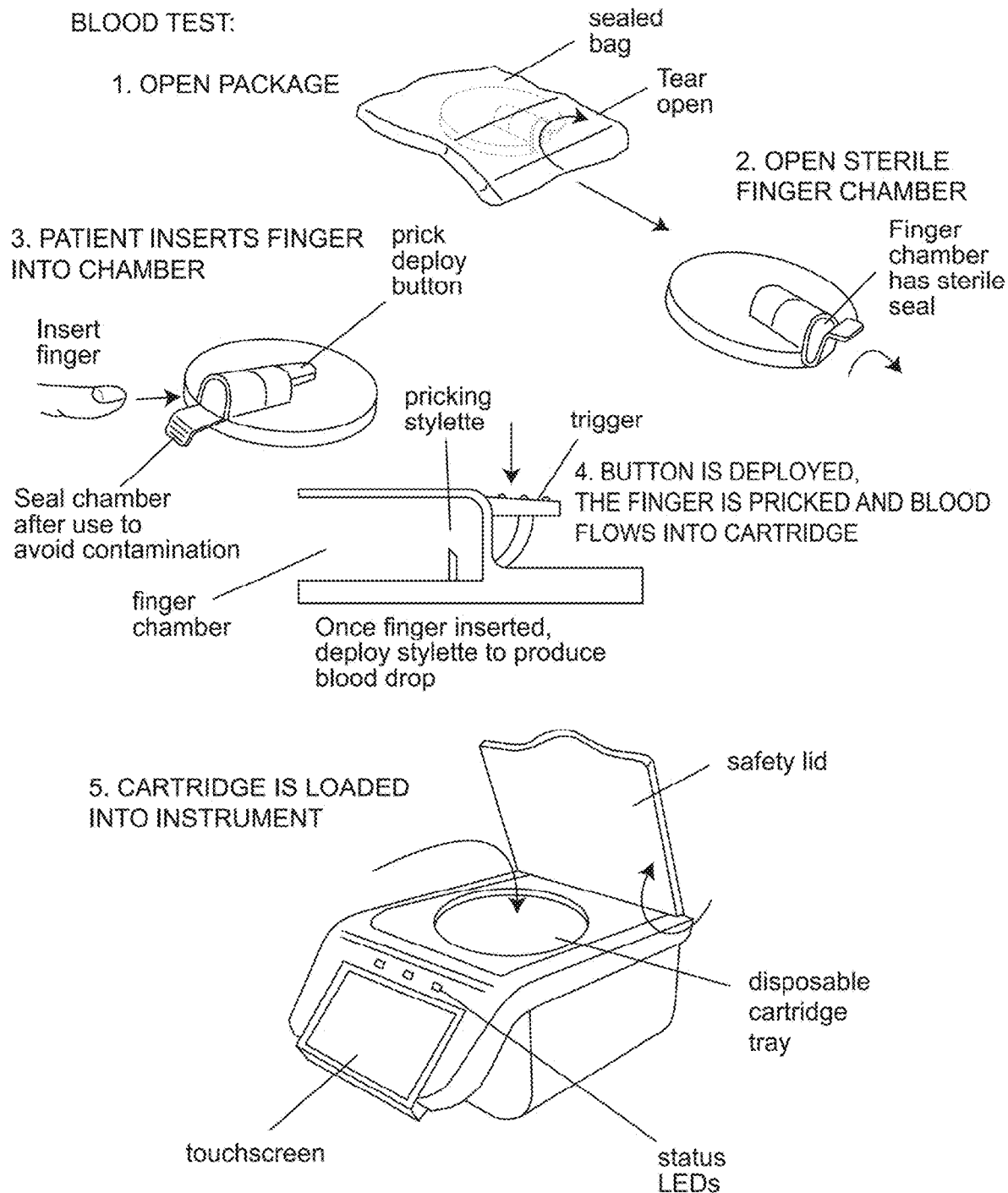
FIG. 13 depicts, in accordance with various embodiments of the present invention, one non-limiting example of a system described herein. This non-liming example applies a blood test.

In some embodiments the sample collector is configured to collect a blood sample from the subject. For example, the blood sample collector comprises a needle and a reservoir to collect the blood. The blood sample collector is configured with a chamber to receive the subject's finger to place the subject's finger in proximity to or in contact with the needle. The blood sample collector can further comprise a button or switch configured to be activated deploy the needle to prick the finger. For example, a button that when pressed triggers the needle to prick the finger and allow the blood to collect in the reservoir. FIG. 13 illustrates one non-limiting example of a system described herein that comprises a blood sample collector. In various embodiments, a capillary flow based device or method is used to collect a blood sample from the subject.

In some embodiments, a system described herein further comprises a sample cartridge configured to hold a biological sample, and to supply the biological sample to at least one inlet of the enzyme reaction module. In various embodiments, a system described herein comprises a sample reservoir or cartridge. Various embodiments of the present invention provide for a sample reservoir or cartridge. The sample reservoir or cartridge can be used to store the sample and/or transfer the sample into an enzyme reaction chamber as described herein. In some embodiments, the sample reservoir or cartridge is part of the sample collector. In other embodiments, the sample reservoir or cartridge is a separate component from the sample collector. In certain embodiments, the sample collector is connected to the sample reservoir or cartridge, and the collected sample is transferred from the sample collector to the sample reservoir or cartridge. In various embodiments, the sample reservoir or cartridge is connected to an enzyme reaction module described herein and transfers the sample into the enzyme reaction module. In certain embodiments, a filtration module is placed between the sample reservoir or cartridge and the enzyme reaction module. In various embodiments, the sample reservoir or cartridge is integrated with an enzyme reaction module described herein and transfers the sample into the enzyme reaction module.

Filtration Module

In various embodiments, the system comprises a filtration module. Various embodiments of the present invention provide for a filtration module. In various embodiments, the filtration module comprises a fluid passage and one or more filters placed on the fluid passage. In some embodiments, the filter or filters have a molecular weight cutoff value of about 1-5, 5-10, 10-20, 20-50 or 50-100 kDa. In some embodiments, the filter or filters have a molecular weight cutoff value of about 3, 5, or 10 kDa. In various embodiments, the filter or filters are made of an organic membrane. In other embodiments, the filter or filters are made of an inorganic membrane. In some embodiments, the filter membrane is made of cellulose acetate (CA), polysulfone, polyvinylidene fluoride, polyethersulfone or polyamide, or any other suitable polymer. In other embodiments, the filter membrane is made of sintered metal or porous alumina.

In various embodiments, the filtration module comprises at least one inlet, through which a biological sample, a reagent or buffer solution, an enzyme solution, a catalyst, and/or a reaction mixture can enter the filtration module. In various embodiments, the filtration module comprises at least one outlet, through which a biological sample, a reagent or buffer solution, an enzyme solution, a catalyst, and/or a reaction mixture can exit the filtration chamber. In various embodiments, the fluid pathway is from the inlet, through the filters, to the outlet.

In one embodiment, a filtration module's outlet is connected to an enzyme reaction module's inlet. In another embodiment, a filtration module's outlet is connected to a sequestration-liberation module's inlet. Still in one embodiment, a filtration module's outlet is connected to a detection module's inlet.

In other embodiments, the filtration module is one or more filters connected to an enzyme reaction module's inlet. In other embodiments, the filtration module is one or more filters connected to a sequestration-liberation module's inlet. In other embodiments, the filtration module is one or more filters connected to a detection module's inlet.

In one embodiment, a filtration module's inlet is connected to the outlet of a sample collector, reservoir or cartridge. In another embodiment, a filtration module's inlet is connected to a sequestration-liberation module's outlet. Still in one embodiment, a filtration module's inlet is connected to a detection module's outlet.

In some embodiments, a filtration module is integrated with an enzyme reaction module, a sequestration-liberation module, and/or a detection module.

Enzyme Reaction Module

Various embodiments of the present invention provide for an enzyme reaction module. In various embodiments, a system described herein comprises an enzyme reaction module. In various embodiments, the enzyme reaction module comprises an enzyme reaction chamber. In one embodiment, the enzyme reaction chamber is formed by an outer shell or casing. In various embodiments, the enzyme reaction module comprises at least one inlet, through which a biological sample, a reagent or buffer solution, an enzyme solution, a catalyst, and/or a reaction mixture enters the enzyme reaction chamber. In various embodiments, the enzyme reaction module comprises at least one outlet, through which a biological sample, a reagent or buffer solution, an enzyme solution, a catalyst, and/or a reaction mixture exit the enzyme reaction chamber. In various embodiments, the fluid pathway is from the inlet, through the enzyme reaction chamber, to the outlet. In various embodiments, the enzyme reaction chamber is configured to conduct a fluid flow from the inlet, through the enzyme reaction chamber, to the outlet.

In various embodiments, at least one inlet of the enzyme reaction chamber is configured to receive a biological sample, enzyme, reagent, buffer, fluid flow, and/or reaction mixture thereinto. In various embodiments, at least of one inlet of the enzyme reaction chamber is configured to receive a quantity of cystathionine synthase and/or a quantity of cystathionine lyase thereinto.

In various embodiments, the enzyme reaction chamber is shaped as a column having a length of about 1-2, 2-5, 5-10, 10-20, 20-50, 50-100, 100-200, 200-500, or 500-1000 mm. In various embodiments, enzyme reaction chamber is shaped as a column having a diameter of about 0.1-0.2, 0.2-05, 0.5-1.0, 1-2, 2-5, 5-10, 10-20, 20-50, or 50-100 mm. In various embodiments, the enzyme reaction module further comprises a heater and/or cooler configured to control the temperature inside the enzyme reaction chamber.

In various embodiments, the enzyme reaction module further comprise a filter along the pathway of the fluid flow, and configured to filter a biological sample, enzyme, reagent, buffer, fluid flow, and/or reaction mixture. In one embodiment, the filter is located before the enzyme reaction chamber. In various embodiments, the device further comprises a prefilter placed on the fluid pathway before, in or after the sample port or inlet, through which the biological sample passes before entering the enzyme reaction chamber.

In some embodiments, the filter and/or prefilter is a 3 kDa filter. In other embodiments, the filter and/or prefilter is a membrane. As a non-limiting example, the membrane can be a polysulfone membrane designed with a plurality of pores embedded in the membrane to capture and/or allow passage of specific biomarkers. Other non-limiting examples of the membrane include sintered metal, porous alumina, cellulose acetate (CA), polyvinylidene fluoride, polyethersulfone, polyamide, and other suitable polymers.

In one embodiment, a filtration module as described in is connected to the inlet of the enzyme reaction module. In another embodiment, a filtration module as described in is connected to the outlet of the enzyme reaction module. Still in another embodiment, the enzyme reaction module's inlet and outlet are each connected to a filtration module. In another embodiment, a filtration module is integrated with the enzyme reaction module.

In various embodiments, the enzyme reaction module comprises one or more enzymes. In various embodiments, the enzyme reaction module is configured to hold one or more enzymes. In various embodiments, the one or more enzymes are cystathionine synthase and/or cystathionine lyase.

In some embodiments, the enzyme reaction module comprises an enzyme reservoir or compartment for holding one or more enzymes therein, wherein the enzyme reservoir or compartment is connected to the enzyme reaction chamber and configured to transfer the one or more enzymes into the enzyme reaction chamber. In other embodiments, the enzyme reservoir or compartment is configured to hold a quantity of cystathionine synthase and/or a quantity of cystathionine lyase therein.

In various embodiments, the reaction chamber is configured to hold one or more enzymes. In some embodiments, the enzyme reaction chamber is configured to hold a quantity of cystathionine synthase therein. In some embodiments, the enzyme reaction chamber is configured to hold a quantity of cystathionine lyase therein. In other embodiments, the enzyme reaction chamber is configured to hold a quantity of cystathionine synthase and a quantity of cystathionine lyase therein. In various embodiments, the enzyme reaction chamber contains one or more enzymes, such as cystathionine synthase and cystathionine lyase.

In various embodiments, one or more of the enzymes held in the enzyme reaction module is in a liquid solution or fluid composition. In various embodiments, one or more of the enzymes held in the enzyme reaction module is immobilized on a solid support, including but not limited to resins, gels, matrices, beads, columns, sheets and other suitable supports. In one embodiment, the solid support is made of agarose, cellulose, alumina, silica gel, magnetic beads, and other suitable sugar- or acrylamide-based polymer resins.

In various embodiments, the reaction chamber comprises no enzyme. In various embodiments, the enzyme reaction module comprises an enzyme port or inlet, through which an enzyme is introduced into the enzyme reaction chamber. In one embodiment, the enzyme is transferred from an enzyme reservoir or compartment of the enzyme reaction module. In another embodiment, the enzyme is transferred from an enzyme cartridge connected to the enzyme reaction module. In one embodiment, cystathionine synthase and/or cystathionine lyase enter before a biological sample enters the reaction chamber. In another embodiment, cystathionine synthase and/or cystathionine lyase enter after a biological sample enters the reaction chamber. Still in another embodiment, cystathionine synthase and/or cystathionine lyase enter concurrently with a biological sample. One of ordinary skill in the art would understand that cystathionine synthase (CS), cystathionine lyase (CL) and a biological sample (S) could take many possible time sequences to enter the reaction chamber, including but not limited to: S, CS, and CL all together; S, then CS and CL together; CS and CL together, then S; S-CS-CL; S-CL-CS; CS-S-CL; CL-S-CS; CS-CL-S; and CL-CS-S. Also in various embodiments, the respective time periods of introducing CS, CL and S into the reaction chamber can be completely separated, partially overlapped, or completely overlapped. In one embodiment, the cystathionine synthase is a cystathionine beta-synthase and/or the cystathionine lyase is a cystathionine gamma-lyase.

Enzyme and Enzyme Cartridge

In various embodiments, the system comprises an enzyme for converting/collapsing methionine metabolites (e.g., homocysteine, cystathionine, and cysteine) to cysteine. In some embodiments, cystathionine synthase and cystathionine lyase is used for this converting/collapsing step. For example, in the enzyme reaction chamber, methionine metabolites are enzymatically converted or collapsed into cysteine.

In one embodiment, the cystathionine synthase is a polypeptide comprising the sequence as set forth in SEQ ID NO:1 or SEQ ID NO:5. In another embodiment, the cystathionine synthase is a polypeptide consisting of the sequence as set forth in SEQ ID NO:1 or SEQ ID NO:5. In one embodiment, the cystathionine lyase is a polypeptide comprising the sequence as set forth in SEQ ID NO:8 or SEQ ID NO:12. In another embodiment, the cystathionine lyase is a polypeptide consisting of the sequence as set forth in SEQ ID NO: 8 or SEQ ID NO:12.

"Cystathionine synthase" as used herein refers to an enzyme that catalyzes the reaction of from homocysteine to cystathionine. In various embodiments, the cystathionine synthase is cystathionine beta-synthase. In accordance with the present invention, "cystathionine beta-synthase" (Registry Number: EC 4.2.1.22; CAS Type 1 Name: L-Serine hydro-lyase (adding homocysteine)) is a well-established term referring to a specific enzyme with the defined function of converting homocysteine to cystathionine. It catalyzes the reaction: L-serine+L-homocysteine<=>L-cystathionine+$H_2O$. Examples of "cystathionine synthase" include but are not limited to polypeptides comprising a sequence as set forth in SEQ ID NO: 1 or SEQ ID NO: 5. Also in accordance with various embodiments of the present invention, the cystathionine synthase can comprise a variant or mutant of the sequence as set forth in SEQ ID NO: 1 or SEQ ID NO: 5. To be noted, SEQ ID NO: 1 and SEQ ID NO: 5 are provided merely as non-limiting examples from the organism Helicobacter pylori to illustrate the invention, and should not be interpreted as limiting the scope of the invention. It is contemplated that cystathionine beta-synthase from many other organisms in addition to Helicobacter pylori can be used in various embodiments of the invention. Cystathionine beta-synthase is known in various organisms, including but not limited to, *Homo sapiens* (UGID:1292388, UniGene Hs.533013), *Mus musculus* (UGID:306640; UniGene Mm.206417), *Rattus norvegicus* (UGID:438413; UniGene Rn.87853), and *Danio rerio* (UGID:2438161;UniGene Dr.76887) etc. The sequences of these known cystathionine beta-synthases are publicly available, for example, on the National Center for Biotechnology Information (NCBI) website.

"Cystathionine lyase" as used herein refers to an enzyme that catalyzes the reaction of from cystathionine to cysteine. In various embodiments, the cystathionine lyase is cystathionine gamma-lyase. In accordance with the present invention, "cystathionine gamma-lyase" (Registry Number: EC 4.4.1.1; CAS Type 1 Name: L-Cystathionine cysteine-lyase (deaminating)) is a well-established term referring to a specific enzyme with the defined function of converting cystathionine to cysteine. It catalyzes the reaction: L-cystathionine+$H_2O$<=>L-cysteine+$NH_3$+2-oxobutanoate. Examples of "cystathionine lyase" include but are not limited to polypeptides comprising a sequence as set forth in SEQ ID NO: 8 or SEQ ID NO: 12. Also in accordance with various embodiments of the present invention, the cystathionine lyase can comprise a variant or mutant of the sequence as set forth in SEQ ID NO: 8 or SEQ ID NO: 12. To be noted, SEQ ID NO: 8 and SEQ ID NO: 12 are provided merely as non-limiting examples from the organism Helicobacter pylori to illustrate the invention, and should not be interpreted as limiting the scope of the invention. It is contemplated that cystathionine gamma-lyase from many other organisms in addition to Helicobacter pylori can be used in various embodiments of the invention. Cystathionine gamma-lyase is known in various organisms, including but not limited to, *Homo sapiens* (UGID:134002; UniGene Hs.19904), *Mus musculus* (UGID:264112; UniGene Mm.28301), *Rattus norvegicus* (UGID:379103; UniGene Rn.3881), and *Danio rerio* (UGID:2438268; UniGene Dr.76994) etc. The sequences of these known cystathionine gamma-lyase are publicly available, for example, on the National Center for Biotechnology Information (NCBI) website.

An example of protein sequence of the cystathionine beta-synthase is SEQ ID NO:1 (Protein: Cystathionine beta-synthase 305 amino acids; Source organism: *Helicobacter pylori* 908; ACCESSION: ADN79248):

```
MILTAMQDAIGRTPIFKFTRKDYPIPLKSAIYAKLEHLNPGGSVKDRLGQ

YLIKEAFRTHKITSTTTIIEPTAGNTGIALALVAIKHHLKTIFVVPEKFS

VEKQQIMRALGALVINTPTSEGISGAIKKSKELAESIPDSYLPLQFENPD

NPAAYYHTLAPEIVKELGTNFTSFVAGIGSGGTFAGTAKYLKERIPNIRL

IGVEPEGSILNGGEPGPHEIEGIGVEFIPPFFANLDIDGFETISDEEGFS

YTRKLAKKNGLLVGSSSGAAFAAALKEVQRLPEGSQVLTIFPDMADRYLS

KGIYS
```

An optimized cystathionine beta-synthase (oCBS, 404 amino acids) can also be used. The optimized enzyme is constructed with codon usage enabling high *E. coli* expression and the addition of a cellulose binding domain for ease of purification with cellulose. The cellulose also can serve as a solid substrate for enzyme reaction.

oCBS nucleotide sequence (1215 bp; SEQ ID NO:2):

```
ATGACCCCGGTGTCTGGCAACCTGAAAGTCGAATTTTACAACTCCAATCC

GTCTGATACCACGAATAGCATTAACCCGCAGTTCAAAGTTACGAACACCG

GCAGCTCTGCGATTGATCTGTCAAAACTGACGCTGCGTTATTACTATACC

GTCGATGGTCAGAAAGACCAAACCTTTTGGTGCGACCATGCGGCCATTAT

CGGTAGTAACGGCTCCTACAATGGCATTACGTCTAATGTCAAAGGCACCT

TCGTGAAAATGAGTTCCTCAACGAACAATGGCGCCGGTGCAGGCGCTATG

ATCCTGACCGCGATGCAGGATGCCATCGGCCGTACGCCGATTTTTAAATT

CACCCGCAAAGACTACCCGATCCCGCTGAAAAGTGCAATTTATGCTAAAC

TGGAACATCTGAATCCGGGCGGCAGCGTGAAAGATCGTCTGGGTCAATAT

CTGATTAAAGAAGCCTTTCGCACGCACAAAATCACCAGCACCACGACCAT

TATCGAACCGACGGCGGGTAATACCGGTATCGCACTGGCCCTGGTTGCCA

TTAAACATCACCTGAAAACCATCTTTGTGGTTCCGGAAAAATTCTCAGTC

GAAAAACAGCAAATCATGCGTGCGCTGGGCGCCCTGGTGATCAACACGC

CGACCTCAGAAGGTATCTCGGGCGCAATTAAAAAATCGAAAGAACTGGCT

GAAAGCATTCCGGATTCTTACCTGCCGCTGCAATTTGAAAACCCGGACAA

TCCGGCAGCTTACTATCATACCCTGGCACCGGAAATTGTGAAAGAACTGG

GCACGAATTTTACCAGCTTCGTTGCTGGTATCGGCTCTGGCGGTACGTTC

GCAGGCACCGCTAAATATCTGAAAGAACGTATTCCGAACATCCGCCTGAT

TGGCGTGGAACCGGAAGGTAGTATTCTGAATGGCGGTGAACCGGGTCCGC

ACGAAATCGAAGGTATTGGCGTTGAATTTATCCCGCCGTTTTTCGCCAAC

CTGGATATTGACGGCTTTGAAACGATTTCAGATGAAGAAGGTTTCTCGTA

TACCCGCAAACTGGCGAAGAAAAACGGTCTGCTGGTTGGCAGCAGCAGCG

GTGCAGCATTTGCAGCTGCGCTGAAAGAAGTTCAGCGTCTGCCGGAAGGC

AGCCAAGTCCTGACCATTTTCCCGGATATGGCGGACCGCTACCTGAGTAA

AGGTATCTATTCCTAA
```

In SEQ ID NO:2, the linker is SEQ ID NO: 3, which is bp 280-297 of SEQ ID:2:

```
GGCGCCGGTGCAGGCGCT
```

In SEQ ID NO:2, the Cellulose Binding Domain is SEQ ID NO: 4, which is bp 1-279 of SEQ ID:2:

```
ATGACCCCGGTGTCTGGCAACCTGAAAGTCGAATTTTACAACTCCAATCC

GTCTGATACCACGAATAGCATTAACCCGCAGTTCAAAGTTACGAACACCG

GCAGCTCTGCGATTGATCTGTCAAAACTGACGCTGCGTTATTACTATACC

GTCGATGGTCAGAAAGACCAAACCTTTTGGTGCGACCATGCGGCCATTAT

CGGTAGTAACGGCTCCTACAATGGCATTACGTCTAATGTCAAAGGCACCT

TCGTGAAAATGAGTTCCTCAACGAACAAT
``` oCBS protein sequence (404 amino acids; SEQ ID NO:5):

```
MTPVSGNLKVEFYNSNPSDTTNSINPQFKVTNTGSSAIDLSKLTLRYYYT

VDGQKDQTFWCDHAAIIGSNGSYNGITSNVKGTFVKMSSSTNNGAGAGAM

ILTAMQDAIGRTPIFKFTRKDYPIPLKSAIYAKLEHLNPGGSVKDRLGQY

LIKEAFRTHKITSTTTIIEPTAGNTGIALALVAIKHHLKTIFVVPEKFSV

EKQQIMRALGALVINTPTSEGISGAIKKSKELAESIPDSYLPLQFENPDN
```

-continued
```
PAAYYHTLAPEIVKELGTNFTSFVAGIGSGGTFAGTAKYLKERIPNIRLI

GVEPEGSILNGGEPGPHEIEGIGVEFIPPFFANLDIDGFETISDEEGFSY

TRKLAKKNGLLVGSSSGAAFAAALKEVQRLPEGSQVLTIFPDMADRYLSK

GIYS*
```

In SEQ ID NO:5, the linker is SEQ ID NO: 6, which is aa 94-99 of SEQ ID:5:

```
GAGAGA
```

In SEQ ID NO:5, the Cellulose Binding Domain is SEQ ID NO: 7, which is aa 1-93 of SEQ ID:5:

```
MTPVSGNLKVEFYNSNPSDTTNSINPQFKVTNTGSSAIDLSKLTLRYYYT

VDGQKDQTFWCDHAAIIGSNGSYNGITSNVKGTFVKMSSSTNN
```

An example of protein sequence of the cystathionine gamma-lyase is SEQ ID NO:8 (Protein: Cystathionine gamma-lyase 378 amino acids; Source organism: *Helicobacter pylori* 908; ACCESSION: ADN79247):

```
MQTKLIHGGISEDATTGAVSVPIYQASTYRQDAIGRHKGYEYSRSGNPTR

FALEELIADLEGGVKGFAFASGLAGIHAVFSLLQSGDHVLLGDDVYGGTF

RLFNKVLVKNGLSCTIIDTSDISQIKKAIKPNTKALYLETPSNPLLKITD

LAQCASVAKDHGLLTIVDNTFATPYCQNPLLLGADIVAHSGTKYLGGHSD

VVAGLVTTNNEALAQEIAFFQNAIGGVLGPQDSWLLQRGIKTLGLRMEAH

QKNALCVAEFLEKHPKVERVYYPGLPTHPNHELAKAQMRGFSGMLSFTLK

NDSEAALFVESLKLFILGESLGGVESLVGIPALMTHACIPKEQREAAGIR

DGLVRLSVGIEHEQDLLEDLEQAFAKIS
```

An optimized cystathionine gamma-lyase (oCGL, 477 amino acids) can also be used. The optimized enzyme is constructed with codon usage enabling high *E. coli* expression and the addition of a cellulose binding domain for ease of purification with cellulose. The cellulose also can serve as a solid substrate for enzyme reaction.

oCGL nucleotide sequence (1434 bp; SEQ ID NO: 9):

```
ATGACGCCGGTGTCTGGCAATCTGAAAGTGGAATTTTACAACAGCAACCC

GAGCGATACGACGAATAGCATCAACCCGCAGTTCAAAGTGACCAACACGG

GTAGCTCTGCGATTGATCTGTCTAAACTGACCCTGCGTTATTACTATACG

GTTGATGGCCAGAAAGACCAAACCTTTTGGTGCGACCATGCGGCCATTAT

CGGTTCTAACGGCAGTTATAATGGTATCACCAGCAATGTGAAAGGCACGT

TCGTTAAAATGAGTTCCTCAACCAACAATGGCGCAGGTGCTGGCGCGATG

CAGACGAAACTGATTCATGGCGGTATCAGCGAAGATGCAACCACGGGTGC

AGTCTCGGTGCCGATTTACCAGGCCAGCACCTATCGTCAAGACGCAATCG

GTCGCCACAAAGGCTACGAATATTCGCGTAGCGGTAACCCGACGCGCTTT

GCACTGGAAGAACTGATTGCGGATCTGGAAGGCGGTGTGAAAGGCTTTGC

CTTCGCATCAGGTCTGGCAGGCATCCATGCTGTTTTCTCGCTGCTGCAAA
```

```
GCGGTGACCACGTCCTGCTGGGCGATGACGTGTACGGCGGCACCTTTCGC

CTGTTCAACAAAGTTCTGGTCAAAAATGGTCTGAGTTGTACCATTATCGA

TACGTCCGACATTTCACAGATCAAAAAAGCGATTAAACCGAACACCAAAG

CCCTGTATCTGGAAACGCCGTCGAATCCGCTGCTGAAAATTACCGATCTG

GCCCAGTGCGCAAGCGTTGCTAAAGATCATGGCCTGCTGACGATCGTGGA

TAACACCTTTGCGACGCCGTACTGTCAAAATCCGCTGCTGCTGGGTGCGG

ATATTGTCGCCCATTCCGGCACCAAATATCTGGGCGGTCACTCAGACGTG

GTTGCCGGTCTGGTTACCACGAACAATGAAGCTCTGGCGCAGGAAATTGC

GTTTTTCCAAAACGCAATCGGCGGTGTGCTGGGTCCGCAGGATAGCTGGC

TGCTGCAACGTGGTATCAAAACCCTGGGCCTGCGCATGGAAGCGCATCAG

AAAAATGCACTGTGCGTTGCTGAATTTCTGGAAAAACACCCGAAAGTGGA

ACGTGTTTACTATCCGGGTCTGCCGACCCATCCGAACCACGAACTGGCCA

AAGCACAAATGCGCGGTTTTTCTGGCATGCTGAGTTTCACGCTGAAAAAT

GATTCTGAAGCAGCTCTGTTTGTGGAAAGTCTGAAACTGTTCATTCTGGG

TGAATCCCTGGGCGGTGTCGAATCACTGGTGGGCATTCCGGCACTGATGA

CCCATGCTTGTATCCCGAAAGAACAGCGTGAAGCGGCCGGTATTCGTGAT

GGCCTGGTTCGCCTGTCTGTCGGCATCGAACACGAACAGGATCTGCTGGA

AGACCTGGAACAGGCGTTTGCGAAAATTAGTTAA
```

In SEQ ID NO:9, the linker is SEQ ID NO: 10, which is bp 280-297 of SEQ ID:9:

```
GGCGCAGGTGCTGGCGCG
```

In SEQ ID NO:9, the Cellulose Binding Domain is SEQ ID NO: 11, which is bp 1-279 of SEQ ID:9:

```
ATGACGCCGGTGTCTGGCAATCTGAAAGTGGAATTTTACAACAGCAACCC

GAGCGATACGACGAATAGCATCAACCCGCAGTTCAAAGTGACCAACACGG

GTAGCTCTGCGATTGATCTGTCTAAACTGACCCTGCGTTATTACTATACG

GTTGATGGCCAGAAAGACCAAACCTTTTGGTGCGACCATGCGGCCATTAT

CGGTTCTAACGGCAGTTATAATGGTATCACCAGCAATGTGAAAGGCACGT

TCGTTAAAATGAGTTCCTCAACCAACAAT
``` oCGL protein sequence (477 amino acids; SEQ ID NO: 12):

```
MVSYKCGVKDGTKNTIRATINIKNTGTTPVNLSDIKVRYWFTSDGENNFV

CDYAAFGTDKVKKKIENSVPGADTYCEISVKGTFVKMSSSTNNGAGAGAM

QTKLIHGGISEDATTGAVSVPIYQASTYRQDAIGRHKGYEYSRSGNPTRF

ALEELIADLEGGVKGFAFASGLAGIHAVFSLLQSGDHVLLGDDVYGGTFR

LFNKVLVKNGLSCTIIDTSDISQIKKAIKPNTKALYLETPSNPLLKITDL

AQCASVAKDHGLLTIVDNTFATPYCQNPLLLGADIVAHSGTKYLGGHSDV

VAGLVTTNNEALAQEIAFFQNAIGGVLGPQDSWLLQRGIKTLGLRMEAHQ

KNALCVAEFLEKHPKVERVYYPGLPTHPNHELAKAQMRGFSGMLSFTLKN
```

-continued

DSEAALFVESLKLFILGESLGGVESLVG1PALMTHACIPKEQREAAGIRD

GLVRLSVGIEHEQDLLEDLEQAFAKIS*

In SEQ ID NO:12, the linker is SEQ ID NO: 13, which is aa 94-99 of SEQ ID:12:

GAGAGA

In SEQ ID NO:12, the Cellulose Binding Domain is SEQ ID NO: 14, which is aa 1-93 of SEQ ID:12:

MVSYKCGVKDGTKNTIRATINIKNTGTTPVNLSDIKVRYWFTSDGENNFV

CDYAAFGTDKVKKKIENSVPGADTYCEISVKGTFVKMSSSTNN

The enzymes can be expressed in *E. coli* following induction with IPTG. The *E. coli* can be lysed and inclusion bodies can be centrifuged. The pelleted inclusion bodies can be washed 6 times and further lysed by sonication. The released enzymes can be denatured with 1 M urea and dialyzed in pH 5.0 HEPES buffer with 10% glycerol. The dialyzed enzymes can be purified with cellulose resin. The enzymes can be eluted from the cellulose with ddH$_2$O.

In some embodiments, a system described herein further comprises an enzyme cartridge configured to hold a quantity of cystathionine synthase and/or a quantity of cystathionine lyase, and to supply the quantity of cystathionine synthase and/or quantity of cystathionine lyase to the enzyme reaction chamber.

In some embodiments the system comprises at least one enzyme cartridge comprising a quantity of one or more enzymes, including but not limited to cystathionine synthase and cystathionine lyase. In one embodiment, the system comprises an enzyme cartridge comprising a quantity of cystathionine synthase. In one embodiment, the system comprises an enzyme cartridge comprising a quantity of cystathionine lyase. In one embodiment, the system comprises an enzyme cartridge comprising a quantity of cystathionine synthase and a quantity of cystathionine lyase. The enzyme cartridge can further comprise serine, pyridoxal phosphate.

In one embodiment, the enzyme cartridge is integrated with and hence a part of the enzyme reaction module, and connected to the enzyme reaction chamber. In another embodiment, the enzyme cartridge is a component separate from the enzyme reaction module, and connected to the enzyme reaction chamber. In various embodiments, the enzyme cartridge can comprise at least one outlet, through which the contents in the enzyme cartridge can exit. In one embodiment, the enzyme cartridge's outlet is connected to an inlet of the enzyme reaction chamber, and the contents of the enzyme cartridge are transferred into the enzyme reaction chamber. The enzyme cartridge's contents can be transferred before, during or after the biological sample enters the enzyme reaction chamber.

Sequestration-Liberation Module

Various embodiments of the present invention provide for a sequestration-liberation module. In various embodiments, a system described herein comprises a sequestration-liberation module. In various embodiments, the sequestration-liberation module comprises a sequestration-liberation chamber. In one embodiment, the sequestration-liberation chamber is formed by an outer shell or casing. In various embodiments, the sequestration-liberation module comprises at least one inlet, through which a biological sample, a reagent or buffer solution, an enzyme solution, a catalyst, and/or a reaction mixture enters the sequestration-liberation chamber. In various embodiments, the sequestration-liberation module comprises at least one outlet, through which a biological sample, a reagent or buffer solution, an enzyme solution, a catalyst, and/or a reaction mixture exits the sequestration-liberation chamber. In various embodiments, the fluid pathway is from the inlet, through the sequestration-liberation chamber, to the outlet. In various embodiments, the sequestration-liberation chamber is configured to conduct a fluid flow from the inlet, through the sequestration-liberation chamber, to the outlet.

In various embodiments, at least one inlet of the sequestration-liberation chamber is configured to receive a biological sample, enzyme, reagent, buffer, fluid flow, and/or reaction mixture thereinto. In various embodiments, at least one inlet of the sequestration-liberation chamber is configured to receive a wash or exchange buffer thereinto.

In various embodiments, the sequestration-liberation chamber is shaped as a column having a length of about 1-2, 2-5, 5-10, 10-20, 20-50, 50-100, 100-200, 200-500, or 500-1000 mm. In various embodiments, the sequestration-liberation chamber is shaped as a column having a diameter of about 0.1-0.2, 0.2-05, 0.5-1.0, 1-2, 2-5, 5-10, 10-20, 20-50, or 50-100 mm. In various embodiments, the sequestration-liberation module further comprises a heater and/or cooler configured to control the temperature inside the sequestration-liberation chamber. In various embodiments, the sequestration-liberation module further comprises a filter located along the pathway of the fluid flow, and configured to filter a biological sample, enzyme, reagent, buffer, fluid flow, and/or reaction mixture. In one embodiment, the filter is located before the sequestration-liberation chamber.

In various embodiments, the sequestration-liberation chamber comprise gold particles inside the sequestration-liberation chamber; and electrodes configured to conduct an electric current through the gold particles. In various embodiments, the electric current conducted through the gold particles is an alternating current (AC) or direct current (DC), or a mixture thereof. In various embodiments, the sequestration-liberation chamber comprises gold plates or foils and electrodes.

In some embodiments, the gold particles have a diameter of about 0.1-0.2, 0.2-05, 0.5-1.0, 1-2, 2-5, 5-10, 10-20, 20-50, 50-100, 100-200, 200-500, or 500-1000 µm, or a mixture thereof. In some embodiments, the gold particle has a diameter of about 0.1, 0.2, 0.3, 0.4, 0.5, 0.6, 0.7, 0.8, 0.9, 1, 2, 3, 4, 5, 6, 7, 8, 9 or 10 µm. The gold particles can be substantially uniform in their diameters, or can be a mixture of gold particles of different diameters.

In some embodiments, the cysteine sequestration/liberation chamber comprises one, two, or more gold plates or foils. In various embodiments, the gold plate or foil has a surface area of about 1-2, 2-5, 5-10, 10-20, 20-50, 50-100, 100-200, 200-500, 500-1000, 1000-2000, 2000-5000, 5000-10000 cm$^2$. In one embodiment, a stacked gold plate or foil's surface area for about 10 µL serum sample containing about 500 µM cysteine and/or methionine metabolite is about 50, 60, 70, 80, 90, 100, 110, 120, 130, 140, or 150 cm$^2$. In one embodiment, increased surface area is achieved by a controlled surface texture.

In some embodiments, the sequestration-liberation chamber comprises two or more electrodes. In one embodiment, the electrodes are configured to conduct alternating current (AC). In another embodiment, the electrodes are configured to conduct direct current (DC). Still in another embodiment, the electrodes are configured to conduct AC and/or DC. In various embodiments, the electrodes are a positive electrode and a negative electrode. In some embodiments, at least one electrode is located at or near the inlet and at least one electrode is located at or near the outlet. In various embodiments, the electrodes are configured to apply a voltage of about 1-2, 2-4, 4-6, 6-8, or 8-10y. In various embodiments, the electrodes are configured to apply a voltage of about 1, 1.5, 2, 2.5, 3, 3.5, 4, 4.5, 5, 5.5, 6, 6.5, 7, 7.5, 8, 8.5, 9, 9.5, or 10 V. In some embodiments, the electrodes are configured to apply a fixed voltage. In other embodiments, the electrodes are configured to apply a variable voltage.

In various embodiments, the sequestration-liberation module comprises a buffer. In various embodiments, the sequestration-liberation module is configured to hold a quantity of buffer. In various embodiments, the buffer is a wash or exchange buffer.

In some embodiments, the sequestration-liberation module comprises a buffer reservoir or compartment for holding a buffer, wherein the buffer reservoir or compartment is connected to the sequestration-liberation chamber and configured to transfer the buffer into the sequestration-liberation chamber. In other embodiments, the sequestration-liberation chamber is configured to hold a quantity of wash or exchange buffer therein.

In various embodiments, the sequestration-liberation chamber comprises no buffer. In various embodiments, the sequestration-liberation module comprises a buffer port or inlet, through which a buffer is introduced into the sequestration-liberation chamber. In one embodiment, the buffer is transferred from a buffer reservoir or compartment of the sequestration-liberation module. In another embodiment, the buffer is transferred from a buffer cartridge connected to the sequestration-liberation module. In one embodiment, the buffer enters before a biological sample enters the sequestration-liberation chamber.

In some embodiments, a system described herein further comprises a power supply configured to supply a voltage to the electrodes. In some embodiments, the power supply supplies an AC voltage. In some embodiments, the power supply supplies a DC voltage. In some embodiments, the power supply supplies a voltage that can be switched between AC and DC. In various embodiments, the power supply supplies a voltage in the range of about 1-2, 2-4, 4-6, 6-8, or 8-10 V. In various embodiments, the power supply supplies a voltage of about 1, 1.5, 2, 2.5, 3, 3.5, 4, 4.5, 5, 5.5, 6, 6.5, 7, 7.5, 8, 8.5, 9, 9.5, or 10 V. In various embodiments, the power supply supplies a voltage for about 1-5, 5-10, 10-20, 20-30, 30-40, 40-50, or 50-60 seconds, 1-5, 5-10, 10-20, 20-30, 30-40, 40-50, or 50-60 minutes. In some embodiments, the voltage remain fixed during the supply time period. In other embodiments, the voltage varies during the supply time period.

Buffers and Buffer Cartridge

In various embodiments, the system comprise a wash or exchange buffer. In one embodiment, the wash or exchange buffer has a pH of about 8-9, 9-10, 10-11, 11-12, 12-13, or 13-14. In another embodiment, the wash or exchange buffer has a pH of about 8, 8.5, 9, 9.5, 10, 10.5, 11, 11.5, 12, 12.5, 13, 13.5, or 14. In various embodiment, the wash or exchange buffer is phosphate buffer, phosphate buffer saline, Tris buffer, or Tris buffered saline.

In some embodiments, a system described herein further comprises at least one buffer cartridge comprising a quantity of one or more buffers, including but not limited to the wash or exchange buffer. In some embodiments, a system described herein further comprises a buffer cartridge configured to hold a wash or exchange buffer, and to supply the wash or exchange buffer to the sequestration-liberation chamber. In one embodiment, the buffer cartridge is integrated with and hence a part of the sequestration-liberation module, and connected to the sequestration-liberation chamber. In another embodiment, the buffer cartridge is a component separate from the sequestration-liberation module, and connected to the sequestration-liberation chamber. In various embodiments, the buffer cartridge comprises at least one outlet, through which the contents in the buffer cartridge exit. In one embodiment, the buffer cartridge's outlet is connected to an inlet of the sequestration-liberation chamber, and the contents of the buffer cartridge are transferred into the sequestration-liberation chamber. The buffer cartridge's contents can be transferred before, during or after the biological sample enters the sequestration-liberation chamber.

Detection Module

Various embodiments of the present invention provide for a detection module. In various embodiments, a system described herein comprises a detection module. In various embodiments, the detection module comprises a detection channel, through which a biological sample, a reagent or buffer solution, an enzyme solution, a catalyst, and/or a reaction mixture flow. In one embodiment, the detection channel is formed by an outer shell or casing. In various embodiments, the detection module comprises at least one inlet, through which a biological sample, a reagent or buffer solution, an enzyme solution, a catalyst, and/or a reaction mixture enters the detection channel. In various embodiments, the detection module comprises at least one outlet, through which a biological sample, a reagent or buffer solution, an enzyme solution, a catalyst, and/or a reaction mixture exits the detection channel. In various embodiments, the fluid pathway is from the inlet, through the detection channel, to the outlet. In various embodiments, the detection channel is configured to conduct a fluid flow from the inlet, through the detection channel, to the outlet.

In various embodiments, at least one inlet of the detection channel is configured to receive a biological sample, enzyme, reagent, buffer, fluid flow, and/or reaction mixture thereinto. In various embodiments, at least one inlet of the detection channel is configured to receive a detection reagent thereinto. In various embodiments, the detection reagent is a fluorescent/colorimetric detection reagent including but not limited to DTNB.

In various embodiments, the detection module comprises a detection reagent. In various embodiments, the detection module is configured to hold a quantity of a detection reagent. In various embodiments, the detection reagent is a fluorescent/colorimetric detection reagent including but not limited to DTNB. In one embodiment, the detection reagent held in the detection module is in a liquid solution or fluid composition.

In some embodiments, the detection module comprises a reagent reservoir or compartment for holding a quantity of a detection reagent, wherein the reagent reservoir or compartment is connected to the detection channel and configured to transfer the detection reagent into the detection channel. In other embodiments, the detection channel is configured to hold a quantity of a detection reagent.

In various embodiments, the detection channel comprises no detection reagent. In various embodiments, the detection module comprises a detection reagent port or inlet, through which a detection reagent is introduced into the detection channel. In one embodiment, the detection reagent is transferred from a detection reagent reservoir or compartment of the detection module. In another embodiment, the detection reagent is transferred from a detection reagent cartridge connected to the detection module. In one embodiment, the detection reagent enters before a biological sample enters the detection chamber.

In various embodiments, the detection channel of the detection module has a width of about 0.1-0.2, 0.2-0.5, 0.5-1, 1-2, 2-5, 5-10, 10-20, 20-50, 50-100, 100-200, 200-500, or 500-1000 mm. In various embodiments, the detection module further comprises a heater and/or cooler configured to control the temperature inside the detection channel. In various embodiments, the detection module further comprises a filter located along the pathway of the fluid flow, and configured to filter a biological sample, enzyme, reagent, buffer, fluid flow, and/or reaction mixture. In one embodiment, the filter is located before the detection channel.

In various embodiments, the detection module comprises a first aperture and a second aperture; the detection channel is located between the first aperture and the second aperture; and the first and second apertures are configured to conduct a light beam from the first aperture, across the detection channel, to the second aperture. In various embodiments, the detection channel, the first aperture, and the second aperture is so configured that the fluid flow (e.g., a biological sample, reaction mixture or calibration solution) in the detection channel and the light beam are perpendicular to each other. In various embodiments, the detection channel, the first aperture, and the second aperture are so configured that the light beam's path inside the fluid flow has a length of about 0.1-0.2, 0.2-0.5, 0.5-1, 1-2, 2-5, 5-10, 10-20, 20-50, 50-100, 100-200, 200-500, or 500-1000 mm.

In various embodiments, the detection module further comprises a light source configured to emit a light beam into the first aperture. Non-limiting examples of the light source include laser, white light, broad band light source, infrared light, UV, and visible light. In certain embodiments, the light source is a UV LED or an integrated xenon light source. In some embodiments, the light source is placed directly before the first aperture. In some embodiments, the light source is not placed directly before the first aperture, but the light beam is directed by a set of optical component (e.g., lens, filters and mirrors) from the light source to the first aperture.

In various embodiments, the detection module further comprises a photo detector or photosensor (e.g., photodiode, bipolar phototransistor, and photosensitive field-effect transistor) configured to detect the light beam transmitted out of the second aperture. In one embodiment, the photo detector or photosensor is configured to generate a current or voltage output (or an impedance/conductivity variation to influence an applied current or voltage) from the detected transmission light. In some embodiments, the photosensor is placed directly after the second aperture. In some embodiments, the photosensor is not placed directly after the second aperture, but the light beam is directed by a set of optical component (e.g., lens, filters and mirrors) from the second aperture to the photosensor.

In various embodiments, an optical filter is placed before the first aperture, where the optical filter filters out those wavelengths outside the absorbed wavelengths to reduce interference. In various embodiments, an optical filter is placed after the second aperture along the light path, where the optical filter filters out those wavelengths outside the absorbed wavelengths to reduce interference. In various embodiments, the detection module further comprises an optical filter and third aperture; the optical filter is located between the second aperture and the third aperture; the second and third apertures are configured to conduct a light beam from the second aperture, across the optical filter, to the third aperture; and the light beam is filtered by the optical filter. In some embodiments, the optical filter is a band pass filter, a long pass filter, a short pass filter, or a notch filter. In various embodiments, the detection module further comprises a photo detector or photosensor (e.g., photodiode, bipolar phototransistor, and photosensitive field-effect transistor) configured to detect the light beam transmitted out of the third aperture. In one embodiment, the photo detector or photosensor is configured to generate a current or voltage output (or an impedance/conductivity variation to influence an applied current or voltage) from the detected transmission light.

In various embodiments, the photo detector or photosensor detects the light beam transmitted out of the second or third aperture, generates a signal output (e.g., a current or voltage), and measures its light intensity, absorption spectrum and/or emission spectrum (i.e., various light signals of the transmission light). In some embodiments, the output signal is correlated with the concentration of a target molecule in the fluid flow in the detection channel. In some embodiments, the change in transmission light intensity, absorption spectrum and/or emission spectrum is correlated with the concentration of a target molecule in the fluid flow in the detection channel.

Also in various embodiments, provided is a method of using a system as described herein: providing the system, providing cystathionine synthase, cystathionine lyase, wash or exchange buffer, and detection reagent; supplying a biological sample obtained from a subject, cystathionine synthase, cystathionine lyase, wash or exchange buffer, and detection reagent into the system; operating the system; and generating a current or voltage output (or an impedance/conductivity variation to influence an applied current or voltage). In one embodiment, the method further comprises using the generated current or voltage output (or an impedance/conductivity variation to influence an applied current or voltage) to calculate a cysteine and/or methionine metabolite level in the biological sample.

In some embodiment, as certain wavelengths of the light beam are absorbed by a target molecule (e.g., cysteine reacted with DTNB or other fluorescent/colorimetric detection reagent) in the fluid flow, at those wavelengths, the light beam has lower intensity when exiting the second or third aperture (i.e., transmission light intensity) than when entering the first aperture. In other embodiments, absorption spectrum and/or emission spectrum of the light beam is changed by a target molecule in the fluid flow, for example, when cysteine molecules and ions aggregate scattered gold nanorods to form linear structures. The changes in light intensity at certain wavelengths, absorption spectrum and/or emission spectrum is detected and quantified by a photo detector or photosensor (e.g., photodiode, bipolar phototransistor, and photosensitive field-effect transistor) placed after the second or third aperture along the light path. In certain embodiments, the light intensity' transmission decrease is positively correlated to the concentration of the target molecule in the fluid flow. In other words, the transmission light intensity is negatively correlated to the concentration of the target molecule in the fluid flow. In other embodiments, a change in absorption spectrum and/or emission spectrum is correlated to the concentration of the target molecule in the fluid flow.

In one embodiment, the photo detector or photosensor is a photodiode configured to convert light into current and/or voltage and measure the transmission light intensity through the fluid flow. More target molecules are in the fluid flow, more light is absorbed by the fluid flow, less light is transmitted to reach the photodiode, and hence less current or voltage is generated by the photodiode. As a result, the photodiode-generated current or voltage is reversely correlated to the target molecule concentration. In some embodiments, a standard curve between the photodiode-generated current or voltage and the target molecule concentration is obtained by calibrating the detection module with a series of solutions having known concentration of the target molecule; and then, the detection module is used to measure an unknown concentration of the target molecule in a biological sample according to the standard curve. In other embodiments, the information of the standard curve is integrated into the detection module or a data storage/analysis module for automatic calculation.

In various embodiments, the detection module is configured to be inserted into a spectrometer's measurement chamber. In various embodiments, the system described herein further comprises a spectrometer having a measurement chamber that is configured to receive the detection module. In various embodiments, a system described herein further comprises a spectrometer comprising a light source and a photosensor, wherein the light source is configured to emit a light beam into the first aperture, and wherein the photosensor is configured to detect the light beam transmitted out of the second and/or third aperture. In various embodiments, a system described herein further comprises a spectrometer configured to emit a light beam into the first aperture and detect the transmission light intensity out of the second and/or third aperture.

Also in various embodiments, provided is a method of using a system as described herein: providing the system, providing cystathionine synthase, cystathionine lyase, wash or exchange buffer, and detection reagent; supplying a biological sample obtained from a subject, cystathionine synthase, cystathionine lyase, wash or exchange buffer, and detection reagent into the system; operating the system; and detecting a transmission light intensity out of the third aperture. In one embodiment, the method further comprises using the detected transmission light intensity to calculate a cysteine and/or methionine metabolite level in the biological sample.

Data Storage and/or Analysis Module

In various embodiments, a system described herein further comprises a data storage and/or analysis module that is connected to the detection module and/or spectrometer, configured to store the current or voltage output (or an impedance/conductivity variation to influence an applied current or voltage), and/or detected light signals, and/or configured to detect a cysteine and/or methionine metabolite level based on the current or voltage output (or an impedance/conductivity variation to influence an applied current or voltage), and/or detected light signals. In some embodiments, the detected light signals comprise changes in light intensity, absorption spectrum and/or emission spectrum. In some embodiments, the data storage and/or analysis module is further configured to predict, diagnose, prognosticate and/or monitor a disease or condition based on the detected cysteine and/or methionine metabolite level; and The disease or condition is a cancer (e.g., prostate, colon, ovarian and breast cancers), cystinuria, cystine stone disease, or cardiovascular disease (e.g., myocardial infarction (MI), coronary artery disease, peripheral vascular disease, atherosclerosis, and vascular occlusive disease).

Detection Reagent and Detection Reagent Cartridge

In various embodiments, the system comprises a detection reagent composition capable of reacting with cysteine to allow for the quantification of cysteine in the biological sample. In one embodiment, the reaction between the detection reagent and cysteine yields a reaction mixture that has optical properties different from the biological sample and the detection reagent mixture. In various embodiments, the reaction between the detection reagent and cysteine creates new molecules, complex and structures that are fluorescent or colorimetric, or have changes in absorption spectrum and/or emission spectrum. As one non-limiting example, the detection reagent is DTNB, which can react with cysteine to form a complex that blocks light in the 410 nm range. Other detection reagents and assay can be found in Guerra et al. (*Cystinuria: description of a simple method of determination and our 5-year clinical experience*, Acta Biomed Ateneo Parmense. 1990; 61(1-2):85-90), El-Brashy et al. (*Colorimetric determination of some amino acids containing a sulfur group*, Pharm World Sci. 1995 Mar. 24; 17(2):54-7), and Schneider et al. (*Colorimetric assay of cystine using noradrenochrome*, Anal. Biochem., April 1968, 23(1):129-131), which are herein incorporated by reference in their entirety as if fully set forth.

As another non-limiting example, the detection reagent is gold nanorods, as cysteine can aggregate gold nanorods to form linear structures that have different absorption spectrum and/or emission spectrum (e.g., a red shift) as compared to scattered nanorods (see US 2014/0045193 and WO 2014/026157, which are herein incorporated by reference in their entirety as if fully set forth). In some embodiments, the detection channel is configured to hold a quantity of nanorods therein. In certain embodiments, the nanorods hold in the detection channel stay inside the detection channel without leaving the detection channel along the fluid flow.

In some embodiments, the composition capable of reacting with cysteine comprises DTNB or a derivative thereof. In other embodiments, the composition capable of reacting with cysteine comprises nanorods. Still in other embodiments, the composition capable of reacting with cysteine comprises ions, including but not limited to $Cu^{2+}$, $Ni^{2+}$, $Zn^{2+}$, $Hg^{2+}$, $Pd^{2+}$, $Pt^{2+}$, $Co^{2+}$, $Cd^{2+}$, and $Ni^{2+}$, which can form coordinate bonds with cysteine bound on the nanorods. In some embodiments, the concentration of $Cu^{2+}$ is in the range of about 0.1-1 or 1-10 mM. In some embodiments, the composition capable of reacting with cysteine comprises HCl. The concentration of HCl is 0.01N or in the range of about 0.1-1 or 1-10 mM. In certain embodiments, the composition (e.g., DTNB) flows through the detection module. In other embodiments, the composition (e.g., DTNB) is collected in the detection module. In other embodiments, the composition (e.g., nanorods) stays inside the detection module. In some embodiments, the detection cartridge is configured to receive the biological sample and placing the biological sample in contact with nanorods; and after a predetermined period of time, the resulting mixture is placed in contact with the ions.

In various embodiments, a system described herein further comprise a detection reagent cartridge configured to hold a detection reagent, and to supply the detection reagent to at least one inlet of the detection channel. In one embodiment, the detection reagent is 5,5'-dithiobis-(2-nitrobenzoic acid (DTNB). Alternatively, disodium 2-nitro-5-thiosulfobenzoate (NTSB) can be used with sodium sulfite, for detection at 412 nm. Both fluorescent and colorimetric detection of cysteine can include the use of glutathione-protected silver nanoclusters as cysteine-selective fluorometric and colorimetric probe (Yuan et al., *Glutathione-protected silver nanoclusters as cysteine-selective fluorometric and colorimetric probe*, Anal Chem. 2013 Feb. 5; 85(3):1913-9). In another embodiment, the detection reagent is a quantity of nanorods. In still another embodiment, the detection reagent is a quantity of ions.

In some embodiments the system comprises at least one detection reagent cartridge comprising a quantity of one or more detection reagents, including but not limited to DTNB, nanorods and ions. In one embodiment, the detection reagent cartridge is integrated with and hence a part of the detection module, and connected to the detection channel. In another embodiment, the detection reagent cartridge is a component separate from the detection module, and connected to the detection channel. In various embodiments, the detection reagent cartridge comprises at least one outlet, through which the contents in the detection reagent cartridge exit. In one embodiment, the detection reagent cartridge's outlet is connected to an inlet of the detection module, and the contents of the detection reagent cartridge is transferred into the detection module and mixed with the biological sample. The detection reagent cartridge's contents can be transferred before, during or after the biological sample enters the detection module. In one embodiment, the system comprises a detection reagent cartridge comprising a quantity of DTNB or a derivative thereof. In one embodiment, the system comprises a detection reagent cartridge comprising a quantity of nanorods, ions and/or HCl.

Nanorods dimensions usually range 1-100 nm, and their aspect ratios (length divided by width) usually range 3-5. Nanorods can be synthesized from metals or semiconducting materials or their combinations. A nanorod has two ends and a linear body between the two ends. The two ends are also called the transverse or shorter ends. Accordingly, the longitudinal surface of the linear body is also called the longitudinal or longer end. The cross section of the linear body can be shaped as a variety of shapes, examples of which include but are not limited to, sphere, rectangular prism, dumbbell, triangle, rectangle, hexagon, or octagon, or a combination thereof. The two ends and the linear body can be made of the same or different materials. For example, a nanorod can be made by capping the two ends of a carbon or an inert metal linear body with two gold caps. Alternatively, one can use longitudinal surface protected nanorods with exposed gold transverse ends (i.e., polymer coated gold nanorods). An "end surface" as used herein refers to the total area of an end plus the 0-10% of the linear body adjacent to the end; as a nanorod has two end surfaces, a "longitudinal surface" as used herein refers to the remaining 80-100% area of the linear body between the two end surfaces. A nanorod can be made of a variety of materials, including but limited to, gold, selenium, cadmium, copper, platinum, palladium, or carbon, or a combination thereof.

Other Components of the System

Various embodiments of the system describe herein can further comprise one or more other component, modules and devices. Components, modules and devices suitable to be included in the system described herein include but are not limited to pressure gauge, electric wires and switches, pump, vacuum, fluid channels or tubes; control module; and data storage and analysis module. For example, a pressure gauge can enable one to monitor the pressures changes in the system; electric wires and switches can connect a power supply to the sequestration-liberation module, detection module, vacuum, pump and/or spectrometer; fluid channels or tubes can connect various components of the system to allow the biological sample, enzyme composition, buffers and detection reagents to flow through the system; pump or vacuum can provide the driving force to push or pull the fluid flow through the system, and control the flow rate of the fluid through the system for each step of the process of detecting cysteine levels and predicting, diagnosing, prognosticating and/or monitoring a disease or condition; a control module can control, streamline and automate all steps from obtaining a biological sample to predict, diagnose, prognosticate and/or monitor a disease or condition; and data storage and analysis module can store the current or voltage output (or an impedance/conductivity variation to influence an applied current or voltage), detected light signals, cysteine level values, can calculate total cysteine amount, and can predict, diagnose, prognosticate and/or monitor a disease or condition based on the detected cysteine and/or methionine metabolite level; and The disease or condition can be a cancer (e.g., prostate, colon, ovarian and breast cancers), cystinuria, cystine stone disease, or cardiovascular disease (e.g., myocardial infarction (MI), coronary artery disease, peripheral vascular disease, atherosclerosis, and vascular occlusive disease).

Gold Cartridge

Figure 1B:
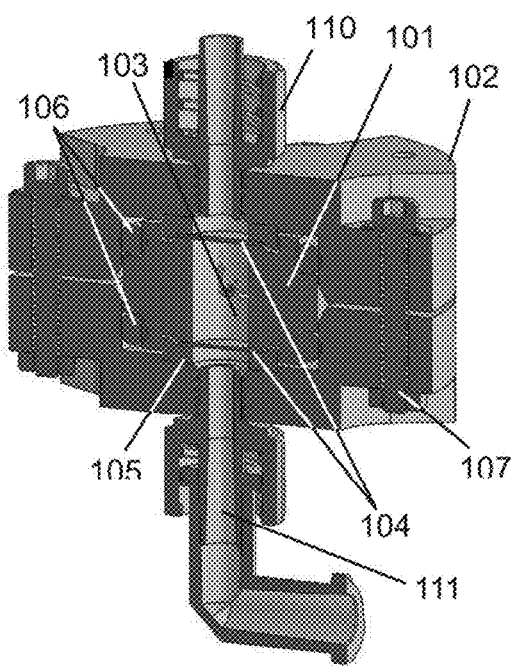

In various embodiments, the cysteine sequestration/liberation module comprises a gold cartridge assembly (e.g., FIGS. 1A-1B).

The gold cartridge assembly comprises a polymeric or plastic hollow cylindrical core 101 made by stereolithography (SLA, a fabrication method) and a machined aluminum outer casing 102. Gold particles of about 1.1 μm diameter are packed within the polymer cylinder 103 and retained on both ends by disks 104 comprised of 80×80 copper mesh and 0.45 μm pore size filter membrane. The copper mesh components are placed directly against both ends of the cylinder, in contact with the gold particles, and the filter membranes are subsequently overlaid on top of the mesh. The two components are held in place by 3D printed caps 105. The SLA core is inserted into the aluminum casing and the interfaces between the parts are sealed using O-rings 106. The two halves of the casing are bolted together using four #3-48 machine screws 107 to maintain the structural integrity of the assembly when subjected to pressure tests. Two electrical wires 108, each soldered at one end to its own copper mesh, pass through the aluminum casing by way of small exit holes 109. These wires are used to apply a voltage across the gold bed to release the cysteine from the gold particles. In some embodiments, the inlet 111 and outlet 110 of the gold cartridge can be threaded to allow the installation of luer fittings.

The purpose of the gold cartridge is to provide a platform for cysteine sequestration, liberation and quantification using a packed bed of gold particles. The cysteine molecules bind to the gold particles as they pass through the gold bed, and are removed from the flow stream. Once all the cysteine-containing fluid is pushed through the gold cartridge, a high pH (>8.5) solution is flushed through the cartridge. At the same time, a voltage is applied across the gold bed through the electrical wires and copper mesh. The electrical current, in combination with the high pH of the solution, liberates the cysteine molecules from the gold. The cysteine then exits the cartridge along with the solution. For testing and calibration, a solution containing a known concentration of cysteine can be applied to the gold cartridge.

In various embodiments, the gold cartridge can be miniaturized to accommodate the small volume of a biological sample from a subject, for example, a finger prick volume of blood or a drop of urine. In some embodiments, the gold cartridge has a thickness/height/length of about 1-2, 2-5, 5-10, 10-20, 20-50, 50-100, or 100-200 mm. In some embodiments, the gold cartridge has a diameter of about 0.1-0.2, 0.2-05, 0.5-1.0, 1-2, 2-5, 5-10, or 10-20 mm.

Filter Cartridge

Figure 2A:
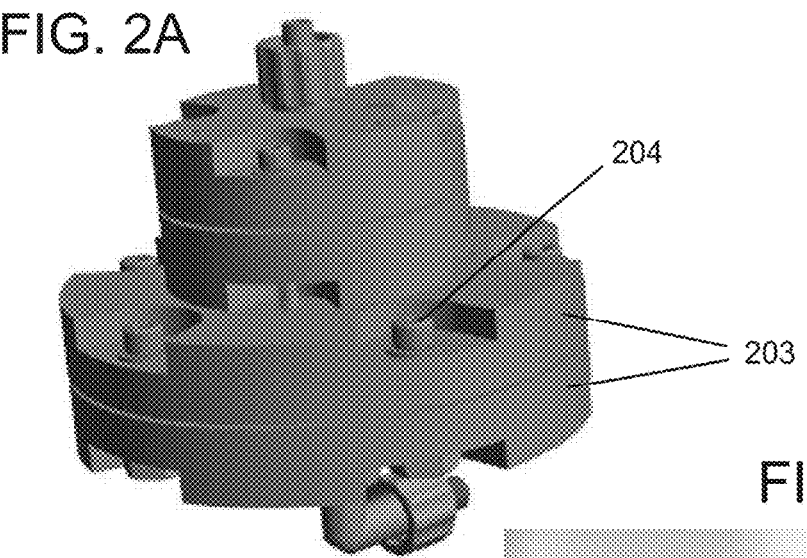
FIGS. 2A-2C depict, in accordance with various embodiments of the present invention, that one non-limiting example of the filter module comprises a filter cartridge assembly.
Figure 2B:
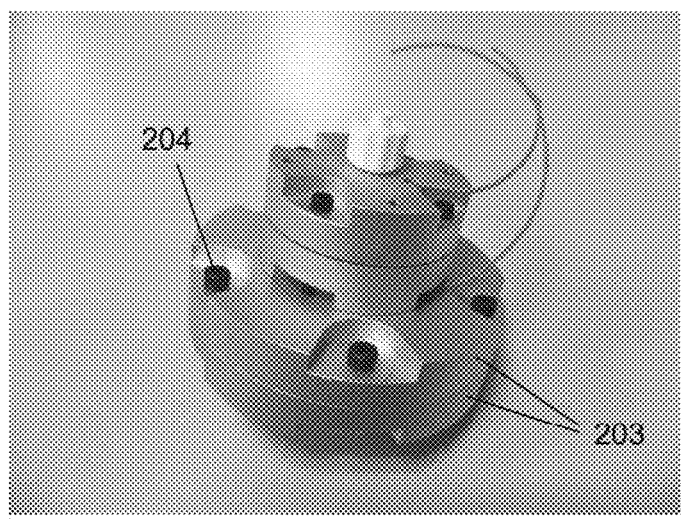
Figure 2C:
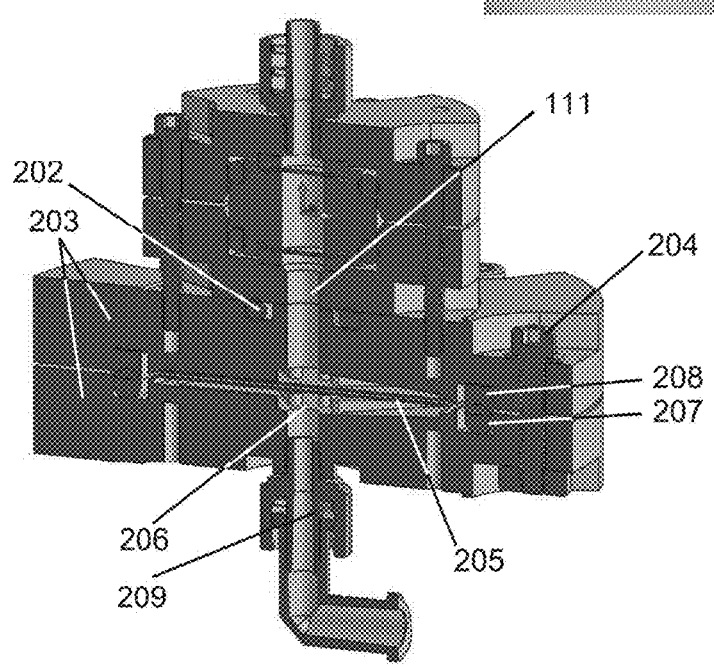

In various embodiments, the filter module comprises a filter cartridge assembly (e.g., FIGS. 2A-2C).

The filter cartridge is designed to be bolted to the inlet of other modules as described herein, including but not limited to enzyme reaction module, cysteine sequestration-liberation module, and cysteine detection module. In the non-limiting example shown in FIGS. 2A-2C, the filter cartridge is bolted to the inlet 111 of the gold cartridge assembly, and the division between both assemblies is sealed by an O-ring 202. The two halves of the machined aluminum filter cartridge casing 203 are bolted together with five #5-40 machine screws 204. A Pall Vivid plasma separation membrane and a Millipore 3 kDa ultrafiltration membrane are separated by a 90+90 stainless steel mesh disk 205, and supported within the filter cartridge by way of radial fins 206. The filter membrane components are held in place and sealed along their perimeter between an O-ring 207 and square ring 208, which are pressed together between the two halves of the casing. The inlet 209 of the filter cartridge can be threaded to allow the installation of a luer fitting.

The purpose of the filter cartridge is to generate filtered plasma from the whole blood sample introduced into the filter cartridge. In one embodiment, for plasma separation, a filter area of 10 cm$^2$ is provided, as per manufacturer specifications (0.04 mL/cm2), to process a 0.4 mL sample of whole blood. The filter cartridge can be tested to determine the suitability of the membrane components types, shapes, areas, sizes, and flow rates, which can then be adjusted according to the test results. In one embodiment, the total dead volume from the inlet to outlet of the cartridge is 2.9 mL, and thus the whole blood sample can be diluted in order to pass all the way through the filters and into the gold cartridge.

In various embodiments, the filter cartridge can be miniaturized to accommodate the small volume of a biological sample from a subject, for example, a finger prick volume of blood or a drop of urine. In some embodiments, the filter cartridge has a thickness/height/length of about 1-2, 2-5, 5-10, 10-20, 20-50, 50-100, 100-200, 200-500, or 500-1000 mm. In some embodiments, the filter cartridge has a diameter of about 0.1-0.2, 0.2-05, 0.5-1.0, 1-2, 2-5, 5-10, 10-20, 20-50, 50-100 mm.

Cysteine Detector Cartridge

Figure 3A:
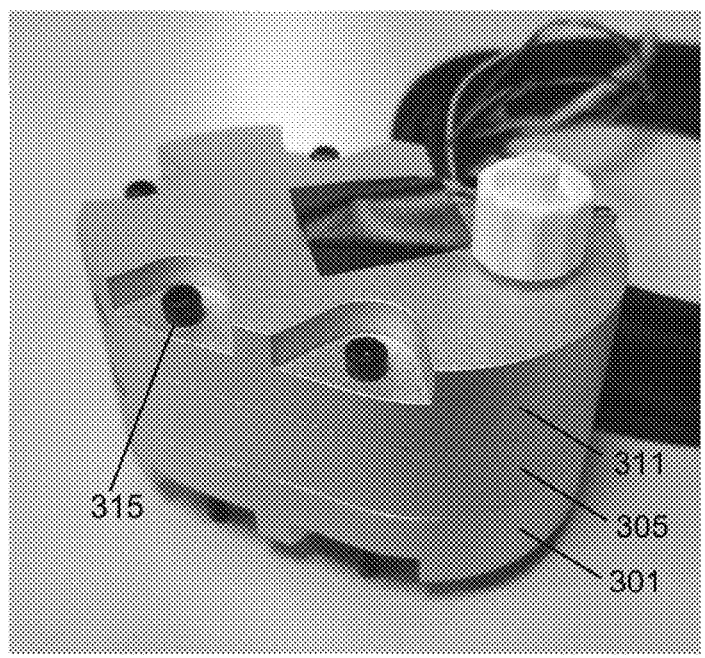
FIGS. 3A-3B depict, in accordance with various embodiments of the present invention, that one non-limiting example of the cysteine detection module comprises a cysteine detector cartridge assembly.
Figure 3B:
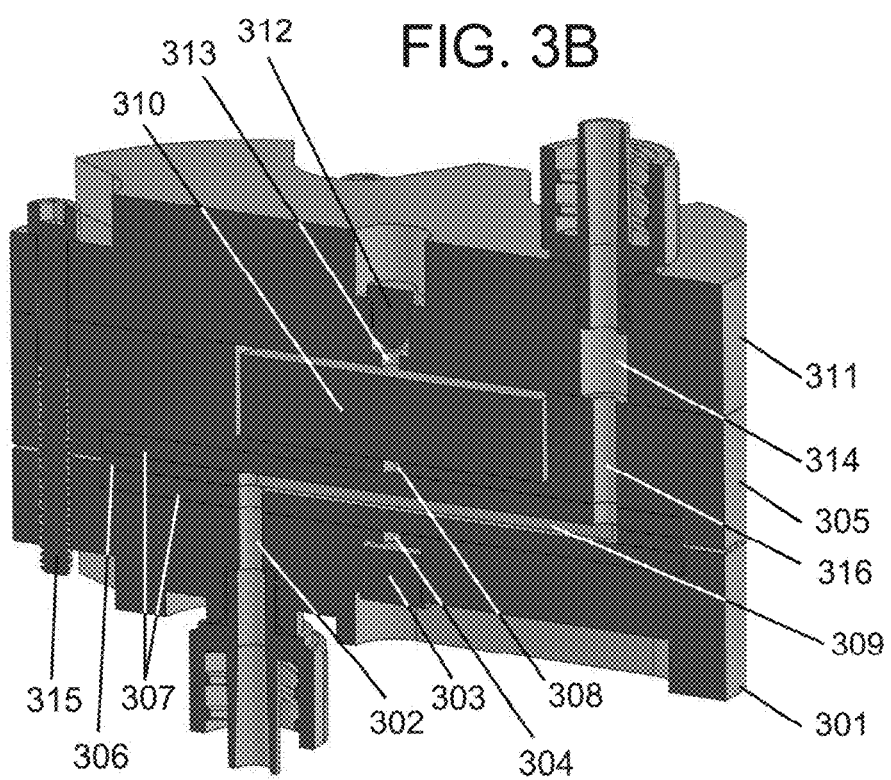

In various embodiments, the cysteine detection module comprises a cysteine detector cartridge assembly (e.g., FIGS. 3A-3B).

The cysteine detector cartridge is composed of three machined aluminum sections. The bottom section 301 features an inlet hole 302 into the cysteine detector, which can line up with the outlet port 110 of the gold cartridge. This section also houses a UV LED 303 that is fixed in place behind a 1 mm diameter aperture 304. Three overlaid slides sit within shallow indentations machined from both the bottom 301 and middle 305 sections of the cartridge. The middle slide 306 is made of 1 mm thick black nylon and has a 2 mm wide slot cut along its central axis. The top and bottom slides 307 are made of 1 mm thick optically clear acrylic and each have a single 2 mm diameter hole that lines up with one of the ends of the channel cut in the middle slide. When stacked, the slides form a microfluidic detection channel 309 that passes directly in between the aperture 304 in the bottom cartridge section and a second aperture 308 in the middle section. In addition, the middle section features a fluid channel 316 and a pocket that holds a band-pass filter 310. Finally, the top section of the cartridge 311 has a mounting hole containing a photodiode 312 in line with a third aperture 313, and an outlet channel 314. All three sections of the cartridge are bolted together using #3-48 machine screws 315.

As activated DTNB (5,5'-dithiobis-(2-nitrobenzoic acid, Ellman's reagent) fluid is pushed through the cysteine detector cartridge, the flow is directed through the microfluidic detection channel 309. UV light, in wavelengths between 380 nm and 440 nm, is emitted by the UV LED 303 and passes through the first aperture 304 and the microfluidic detection channel 309. In the presence of cysteine, the DTNB binds to it and form a complex that blocks light in the 410 nm range. The alternative use of disodium 2-nitro-5-thiosulfobenzoate (NTSB) would similarly block light in the 410 nm range. Higher concentrations of cysteine in the flow result in less light in the 410 nm range passing through the microfluidic detection channel 309. The remaining UV light proceeds through the second aperture 308 and through the band-pass filter 310 which trims out wavelengths that are not within in the 400-425 nm range (ambient light). The resulting light passes into the photodiode 312 which emits a voltage proportional to the intensity of light that is detected. In general, the more cysteine in the fluid, the less light gets through to the diode, producing an attenuated output from the photodiode. As a result, the intensity of the output signal from the photodiode is inversely related to concentration of cysteine in the fluid.

In various embodiments, the detection cartridge can be miniaturized to accommodate the small volume of a biological sample from a subject, for example, a finger prick volume of blood or a drop of urine. In some embodiments, the detection cartridge has a thickness/height/length of about 1-2, 2-5, 5-10, 10-20, 20-50, 50-100, or 100-200 mm. In some embodiments, the detection cartridge has a diameter of about 0.1-0.2, 0.2-05, 0.5-1.0, 1-2, 2-5, 5-10, or 10-20 mm.

Apparatus

Figure 4A:
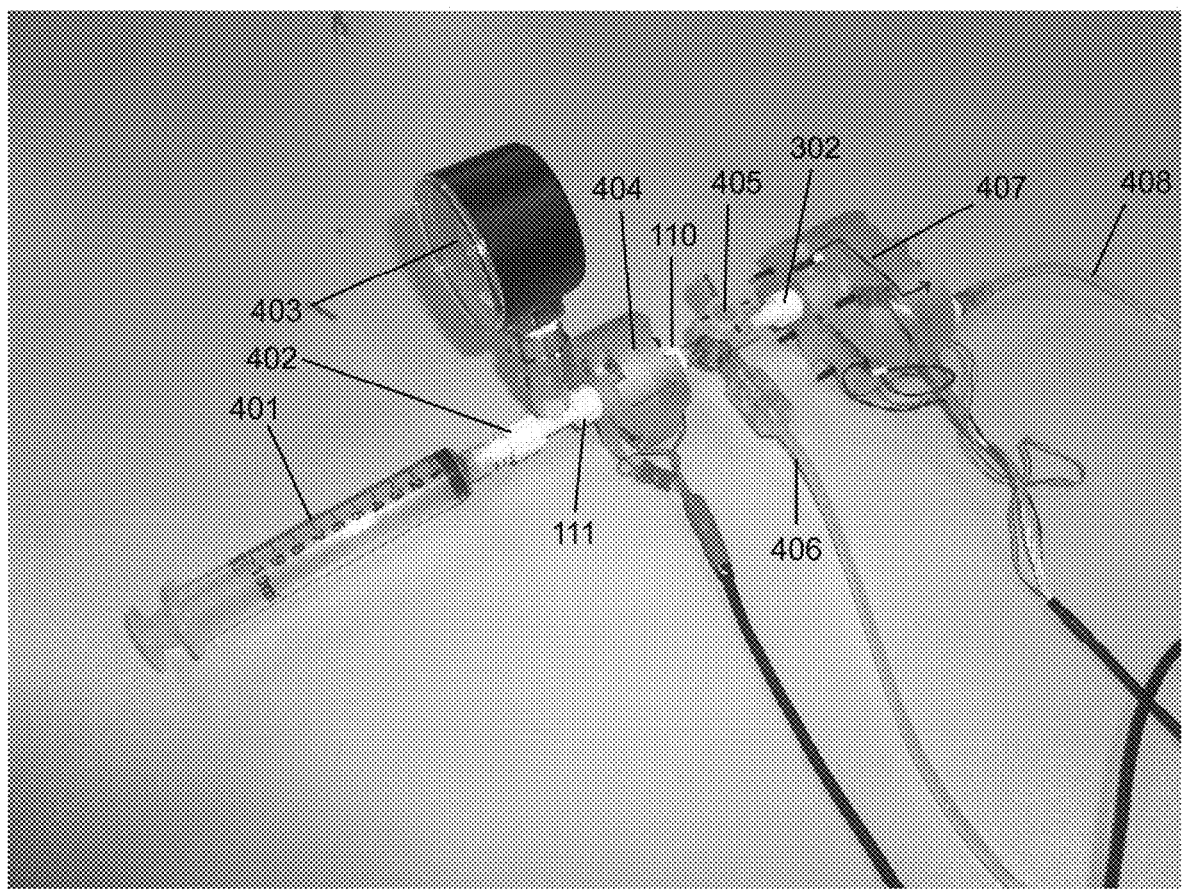
FIGS. 4A-4B depict, in accordance with various embodiments of the present invention, that one non-limiting example of the system described herein comprises an apparatus set up with various modules described herein.
Figure 4B:
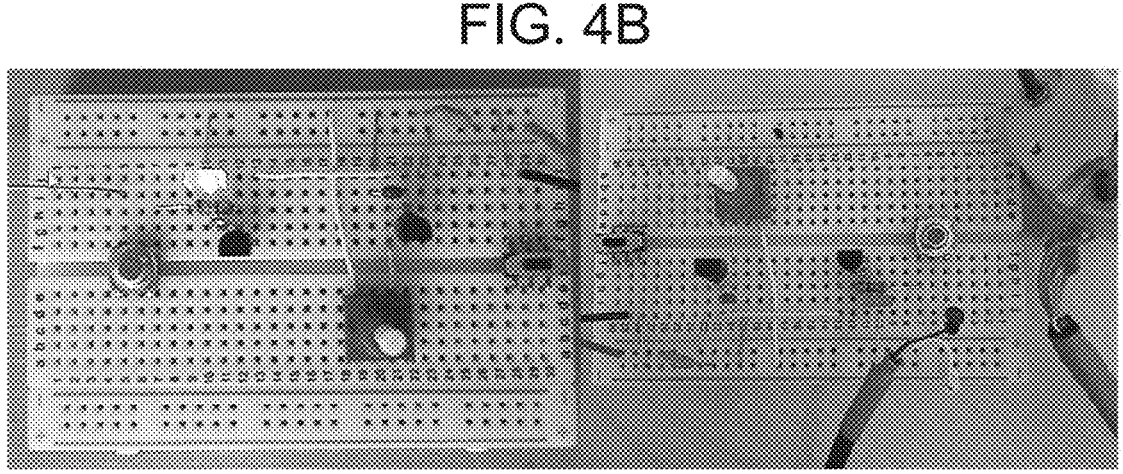

In various embodiments, the system described herein comprises an apparatus set up as shown in FIGS. 4A-4B.

In FIG. 4A, from left to right, the system begins with a 10 mL syringe 401 that is connected to a T-junction 402 which is also connected to both a pressure gauge 403 and the inlet of the gold cartridge 111. The outlet 110 of the gold cartridge 404 is connected to a three-way cock valve 405 which is attached to one end of the DTNB injection tube 406 and the inlet 302 of the cysteine detector cartridge 407. Finally, an outlet tube 408 is hooked up to the outlet of the detector cartridge 407. Electrical wires run from the gold cartridge and detector cartridge to the cysteine dissociation circuit and DTNB detector circuit, respectively.

In some embodiments, various components (including but not limited to wires and switches) of the system are populated on a breadboard for ease of configuration (FIG. 4B). In other embodiments, they can form a simple and compact detection apparatus. Also in various embodiments, they can be miniaturized and integrated to form a single unit so as to accommodate the small volume of a biological sample from a subject, for example, a finger prick volume of blood or a drop of urine. In some embodiments, the single unit is single-use or disposable. In some embodiments, the single unit has a thickness/height/length of about 1-2, 2-5, 5-10, 10-20, 20-50, 50-100, 100-200, 200-500, or 500-1000 mm. In some embodiments, the single unit has a diameter of about 0.1-0.2, 0.2-05, 0.5-1.0, 1-2, 2-5, 5-10, 10-20, 20-50, 50-100 mm.

The detector cartridge can be calibrated prior to running any tests with the gold cartridge. To facilitate calibration, the cock valve can be used to block flow to the gold bed by turning the "OFF" tab towards the outlet of the gold cartridge. Known concentrations of cysteine with DTNB can then be pushed through the DTNB tube to establish standard curve signals from the detector. The brightness of the LED inside the detector can be changed to adjust the intensity and range of the output signals to increase sensitivity.

To run an assay, a cysteine-containing syringe is loaded into the syringe pump which pushes the fluid out of the syringe and into the inlet of the gold cartridge. The pressure gauge is used to monitor the pressure at the inlet of the gold cartridge. In some embodiments, the syringe can be replaced with a pump to push the fluid through the apparatus. In other embodiments, a vacuum can be placed at the exiting end of the apparatus to pull the fluid through the apparatus.

As the fluid moves through the gold cartridge, the cysteine molecules attach to the surface of the gold particles, and cysteine molecules are effectively being removed from the flow. The remaining fluid passes out of the gold cartridge towards the three-way cock valve. At this point, DTNB-containing solution is introduced to the stream through the DTNB tube at a constant flow rate. The combined stream enters the detector cartridge for analysis. In one exemplary case (FIG. 5), all cysteine molecules are sequestered in the gold cartridge and so none is available to form DTNB-cysteine complexes. As a result, the detector cartridge does not detect a difference in cysteine concentration (FIG. 5, Phase A). Once all the cysteine-containing fluid has been injected into the system, a syringe containing a high pH (>8.5) solution is loaded into the syringe pump. This new solution is flushed through the system to ensure that all the cysteine-containing fluid has passed through the gold cartridge.

Once a biological sample has been flushed through the gold cartridge and replaced by the high pH solution, a voltage is applied across the gold particle bed using the cysteine dissociation circuit. The high pH environment, in addition to the voltage, releases the cysteine molecules from the gold into the fluid stream exiting the gold cartridge. At the junction where DTNB is introduced, the later reacts with the cysteine to produce cysteine-DTNB complexes. As the complexes travel through the detector cartridge, the output voltage signal decreases sharply from the baseline value, indicating a rapid increase in cysteine concentration in the flow (FIG. 5, Phase B). While FIG. 5 shows one situation, FIG. 6 shows possible scenarios that can occur on the curve of cysteine concentration.

Plotting the concentration of cysteine over time and multiplying the known constant flow rate by the area under the curve subsequent to the application of voltage (grey area in FIG. 5) give the total amount of cysteine released by the gold cartridge. This value can then be compared to the known quantity of cysteine that was initially introduced into the system.

In another scenario, the collection of the entire high pH solution (which now contains the released cysteine reacted by DTNB) can be made (e.g., a bolus is collected) and then quantified to determine the cysteine concentration in the collected bolus.

When running fluid through the gold cartridge, the pressure on the inlet of the cartridge gradually increases until it eventually reaches steady state. In general, the steady state pressure rises with increases in flow rate. Results obtained in these experiments and background calculations suggest that the inlet pressure can be kept below 30 psi to avoid inlet and outlet filter damage, excessive gold particle packing and leakage. In one embodiment, a flow rate of 0.1mL/min produces a steady state pressure of approximately 7 psi from initial testing.

In addition, air bubbles within the gold cartridge can produce significant increases in pressure since air can have difficulty passing through the wet filter membranes. To minimize air bubbles in the cartridge, end caps are placed on each side of the cartridge to stop the gold bed from drying out when not in use.

Tests can be conducted to adjust the flow rate, solution pH values, voltage and current values. The effectiveness of a gold bed to sequester cysteine can be monitored and evaluated.

Columnar Device

Figure 7:
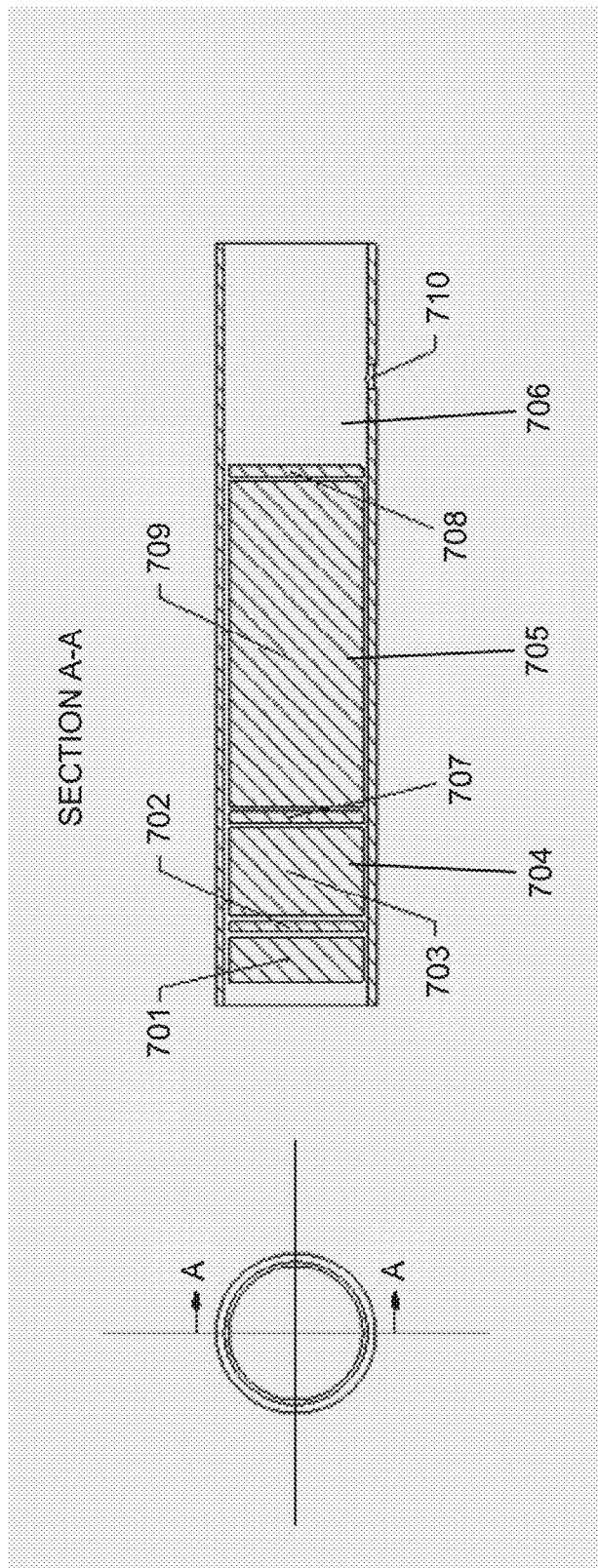
FIG. 7 depicts, in accordance with various embodiments of the present invention, a columnar device comprised three components: enzyme reaction Chamber 1, electro-sequestration and liberation Chamber 2, and cysteine fluorescent/colorimetric detection Chamber 3.

In various embodiments, the filtration, enzyme reaction, sequestration-liberation, and/or detection modules is provided as an integral part, for example, a single use or disposable processing cartridge. As such, in some embodiments, the system described herein may comprise a columnar device set up as shown in FIG. 7 (left panel is cross section view, and right panel is longitudinal section view). The columnar device can be miniaturized to accommodate the small volume of a biological sample from a subject, for example, a finger prick volume of blood or a drop of urine. In some embodiments, the columnar device has a length of about 1-2, 2-5, 5-10, 10-20, 20-50, 50-100, 100-200, 200-500, or 500-1000 mm. In some embodiments, the columnar device has a diameter of about 0.1-0.2, 0.2-05, 0.5-1.0, 1-2, 2-5, 5-10, 10-20, 20-50, 50-100 mm.

The columnar device may comprise three tandem chambers. Chamber 1 (704) is an enzyme reaction chamber containing enzymes (703, e.g., cystathionine synthase and lyase) for collapsing methionine metabolites to cysteine. Chamber 2 (705) is a sequestration-liberation chamber containing gold particles (709) and electrodes (e.g., a pair of positive electrode (707) and negative electrode (708)) for capturing and releasing cysteine. Chamber 3 (706) is a detection chamber for fluorescent/colorimetric detection of cysteine, and it may have an injection port (710) for injecting various reagents, for example, DTNB. The columnar device may also comprise a prefilter (701) and a 3 kDa filter (702) placed before the enzyme reaction chamber.

A biological sample (e.g., serum, whole blood, or urine) can be passed through the device by using a dual syringe pump to maintain constant flow of the sample. A prefilter can be placed in the device. In one embodiment, the prefilter is 3 kDa filter. In another embodiment, the prefilter is a membrane. As such, the membrane can be a polysulfone membrane designed with a plurality of pores embedded in the membrane to capture and/or allow passage of specific biomarkers. For example, the membrane can have a plurality of pore sizes based on the size of the biomarkers that need to be captured and/or passage through the membrane. Also in accordance with various embodiments of the present invention, the device comprises a 3 kDa filter placed after the prefilter.

Following filtration through the prefilter (701) and the 3 kDa filter (702), the sample passes into Chamber 1 (704). In one embodiment, Chamber 1 (704) contains enzymes (703). In another embodiment, enzymes (703) are injected into Chamber 1 (704) via an injection port. The sample is incubated with the enzymes for a predetermined amount of time, and the enzymes collapse methionine metabolites to cysteine.

Once the enzymatic reaction is completed, the sample passes into Chamber 2 (705) that is packed with gold particles (709) such as gold nanoparticles and/or gold microspheres. In another embodiment, Chamber 2 (705) is installed with gold plates or foils. In such an embodiment, a first gold plate or foil is attached to a first wall of Chamber 2 (705) and a second gold plate or foil is attached to a second wall of Chamber 2 (705). Thus, the first gold plate or foil can be parallel to the second gold plate or foil.

As the sample flows through Chamber 2 (705), cysteine binds to the surfaces of the gold particles or plates or foils. A wash and/or exchange buffer is applied to Chamber 2 (705). In one embodiment, the wash and/or exchange buffer is at pH 8.5, whereas the incubation buffer is at pH 5.5. After Chamber 2 (705) is washed and/or exchanged, an electrical charge is applied to the second chamber in order to release cysteine off the gold particles and/or plates or foils. In one embodiment, a positive electrode (707) is positioned at the front aperture of Chamber 2 (705) and a negative electrode (708) is positioned at the back aperture of Chamber 2 (705). The positioning of the electrodes may allow an electrical current to pass through Chamber 2 (705). For example, a voltage of 7.5V can break the cysteine off the gold particles and/or plates or foils. In another embodiment, the voltage can be in the range of about 1-2, 2-4, 4-6, 6-8, or 8-10V. In yet another embodiment, the duration of the electrical current may range from 2 to 10 minutes.

Following application of the electrical current, the effluent including released cysteine, passes into Chamber 3 (706) to react with fluorescent/colorimetric detection reagents, and the resultant fluorescent/colorimetric end products are detected by a spectrometer to quantify cysteine levels. The spectrometer may comprise a photo detector or photosensor such as photodiode, bipolar phototransistor, and photosensitive field-effect transistor, and a light source such as a LED light source, a UV light source, or any other suitable light source. In one embodiment, the photo detector or photosensor is configured to generate a current or voltage output (or an impedance/conductivity variation to influence an applied current or voltage) from the detected transmission light.

In one embodiment, the effluent is sensed using a fluorescent/colorimetric detection agent or media. The fluorescent/colorimetric detection agent or media can be DTNB, for example. The fluorescent/colorimetric detection agent or media can be introduced into Chamber 3, via an injection port (710) on Chamber 3 (706), using a syringe pump. The syringe pump can assist in maintaining a constant flow rate for the chamber system. Once the fluorescent/colorimetric detection agent or media is introduced to Chamber 3 (706), the spectrometer detects cysteine in the effluent. In order to detect the quantity of cysteine in the effluent, the effluent and fluorescent/colorimetric detection agent or media may have a reaction time of 2-10 seconds. In another embodiment, the spectrometer detects the quantity of cysteine in the effluent dynamically.

In one embodiment, DTNB and a series of standard solutions containing known concentration of cysteine is used to calibrate Chamber 3 (706) and the spectrometer, and to obtain a standard curve between cysteine concentrations and the transmission light intensities detected by the spectrometer. The cysteine concentration is higher, more DTNB-cysteine complex forms, more light is absorbed, less light transmits from the light source into the photosensor, the photosensor generates lower voltage, and hence the spectrometer detects lower transmission light intensity. After calibration, Chamber 3 (706) and the spectrometer are used to measure an unknown concentration of cysteine in a sample: using Chamber 3 (706) to react the sample with DTNB, using the spectrometer to detect transmission light intensity of Chamber 3 (706), and using the detected transmission light intensity and the standard curve from calibration to determine the cysteine concentration in the sample.

Finally, the device can output data, including the quantity of cysteine, via a connection to a computer and/or workstation for predicting prostate, colon, ovarian or breast cancer recurrence and making an informed decision in surgical, radiation and adjuvant therapy for prostate, colon, ovarian or breast cancer patients. In one embodiment, the device is connected wirelessly to the computer and/or workstation. Also, the quantified cysteine levels and prognosis results can be printed, displayed on a display component such as a monitor, and communicated to a physician.

Methods of Use

Various embodiments of the present invention also provide for a method of using a system, component, module and/or device described herein. In various embodiments, the method comprises: obtaining a biological sample from a subject; providing a system, component, module and/or device described herein; transferring the biological sample into the system, component, module and/or device; and using the system, component, module and/or device to measure or detect a cysteine and/or methionine metabolite level in the biological sample.

In various embodiments, the method further comprises predicting the risk or probability of cancer recurrence in the subject based on the detected or measured cysteine and/or methionine metabolite level. In various embodiments, the method further comprises prognosticating or diagnosing a cancer in the subject based on the detected or measured cysteine and/or methionine metabolite level. In various embodiments, the recurrence is biochemical recurrence. In various embodiments, the cancer is prostate, colon, ovarian or breast cancer. In various embodiments, the method further comprises predicting, detecting, diagnosing, prognosticating and/or monitoring cystinuria or cystine stone disease in the subject based on the detected or measured cysteine and/or methionine metabolite level. For example, monitoring of urine cysteine levels would allow a patient to correct dietary or other environment factors, and to normalize cysteine levels in order to reduce or prevent stone formation. In various embodiments, the method further comprises predicting the risk or probability of a cardiovascular disease in the subject based on the detected or measured cysteine and/or methionine metabolite level. In various embodiments, the method further comprises predicting, diagnosing, prognosticating and/or monitoring a cardiovascular disease in the subject based on the detected or measured cysteine and/or methionine metabolite level. In some embodiment, the cardiovascular disease is myocardial infarction (MI), coronary artery disease, peripheral vascular disease, atherosclerosis, and/or vascular occlusive disease. In various embodiments, the method further comprises predicting, diagnosing, prognosticating and/or monitoring a disease or condition based on the detected cysteine and/or methionine metabolite level. In various embodiments, the disease or condition is a cancer (e.g., prostate, colon, ovarian and breast cancers), cystinuria, cystine stone disease, or cardiovascular disease (e.g., myocardial infarction (MI), coronary artery disease, peripheral vascular disease, atherosclerosis, and vascular occlusive disease).

Various embodiments of the present invention provide for a method for detecting a cysteine and/or methionine metabolite level in a biological sample from a subject. The method consist of or comprise: providing a system described herein; providing cystathionine synthase, cystathionine lyase, wash or exchange buffer, and detection reagent; obtaining a biological sample from a subject; supplying the biological sample, cystathionine synthase, cystathionine lyase, wash or exchange buffer, and detection reagent into the system; operating the system; and detecting a cysteine and/or methionine metabolite level in the biological sample. In various embodiments, the method further comprises predicting, diagnosing, prognosticating and/or monitoring a condition based on the detected cysteine and/or methionine metabolite level. In various embodiments, the condition is a cancer (e.g., prostate, colon, ovarian and breast cancers), cystinuria, cystine stone disease, or cardiovascular disease (e.g., myocardial infarction (MI), coronary artery disease, peripheral vascular disease, atherosclerosis, and vascular occlusive disease).

In various embodiments, the method further comprises predicting an increased risk or probability of cancer recurrence in the subject when the detected cysteine and/or methionine metabolite level in the subject is higher than a reference cysteine and/or methionine metabolite level. In some embodiments, the reference cysteine and/or methionine metabolite level is a mean or median cysteine and/or methionine metabolite level in non-recurrent subjects detected by the same method.

In various embodiments, the method further comprises predicting an increased risk or probability of cystinuria or cystine stone disease in the subject when the detected cysteine and/or methionine metabolite level in the subject is higher than a reference cysteine and/or methionine metabolite level. In some embodiments, the reference cysteine and/or methionine metabolite level is a mean or median cysteine and/or methionine metabolite level in cystinuria-free and/or cystine stone-free subjects detected by the same method.

In various embodiments, the method further comprises predicting an increased risk or probability of a cardiovascular disease in the subject when the detected cysteine and/or methionine metabolite level in the subject is higher than a reference cysteine and/or methionine metabolite level. In some embodiments, the reference cysteine and/or methionine metabolite level is a mean or median cysteine and/or methionine metabolite level in cardiovascular disease-free subjects detected by the same method. In various embodiments, the reference cysteine and/or methionine metabolite level is a mean or median cysteine and/or methionine metabolite level in asymptomatic subjects detected by the same method. In some embodiments, the reference cysteine and/or methionine metabolite level is a mean or median cysteine and/or methionine metabolite level in healthy subjects detected by the same method.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Figure 8:
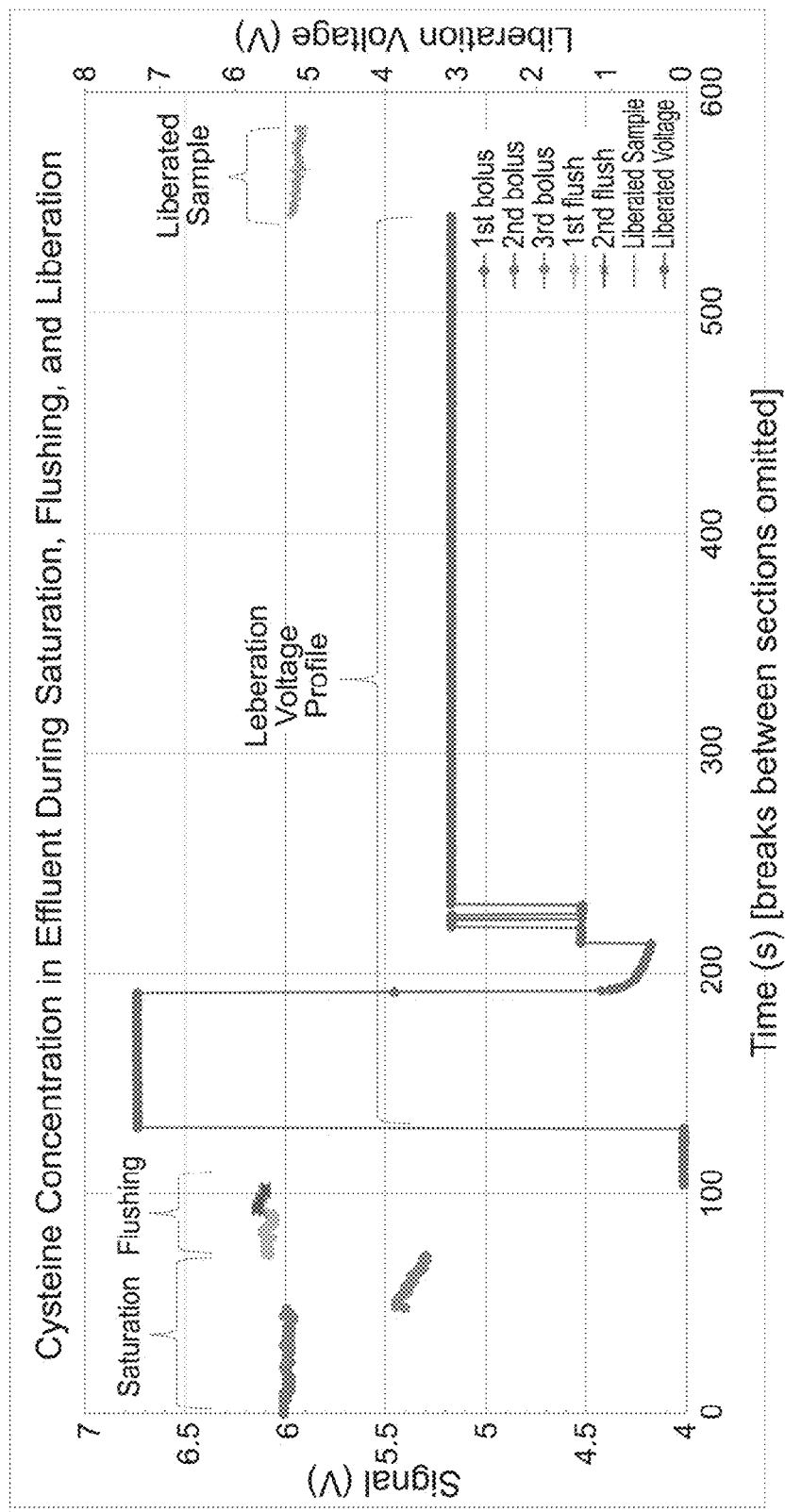
FIG. 8 depicts, in accordance with various embodiments of the present invention, sequestration-liberation runs through the gold cartridge assembly.

As shown in FIG. 8, a gold cartridge was tested for sequestration of cysteine and subsequent liberation via applied voltage. The gold bed was flushed with 400 µM cysteine solution at a rate initially at 10 µl/min. Numerous tiny bubbles were seen exiting the gold bed (presumably trapped air) for the first approximately 5 minutes. Once the air was flushed out, the pressure drop across the bed decreased and the flow gradually increased to 289 µl/min to keep a pressure drop between 20 and 30 psi. During this flushing with 400 µM cysteine, three samples of the effluent were collected and tested for cysteine concentration. The first two samples showed very little cysteine, probably about 50 µM. The concentration in the third sample was noticeably higher, about 100 µM or more, suggesting that the gold bed was approaching saturation. Tris buffer of pH 8.51 was then flushed through the gold bed at 430 µl/min to clear out unbound cysteine. After about 5 ml of buffer had flowed, a sample was tested for cysteine concentration. It was less than 25 µM. An additional 5 ml of buffer was flushed through and the second test again showed less than 25 µM cysteine. Without interrupting the 439 ul/min flow of Tris buffer of pH 8.51, a liberation voltage of about 7.3 V was applied for 60 seconds, followed by 3.1 V for the remainder of the experiment (there were about 30 seconds between the 7.3V and 3.1 V when the voltage varied due to switching the levels). Starting at the first moment when 7.1 V was applied, and continuing for the next approximately 4 minutes, a sample was collected of the effluent. About 1.6 ml had flowed out since the application of the voltage, which was tested for cysteine concentration. The sensor voltage indicated the concentration was between 50 and 100 µM, i.e., it was greater than during the first two boluses that were loading the bed, and much greater than that of the buffer when flushing. 2 mM DTNB has less transmission than 25 µM reacted cysteine; therefore, it can be adjusted that the concentration in the tested solution is not much more than the cysteine concentration, to avoid DTNB over influencing the UV transmission.

Example 2

Figure 9:
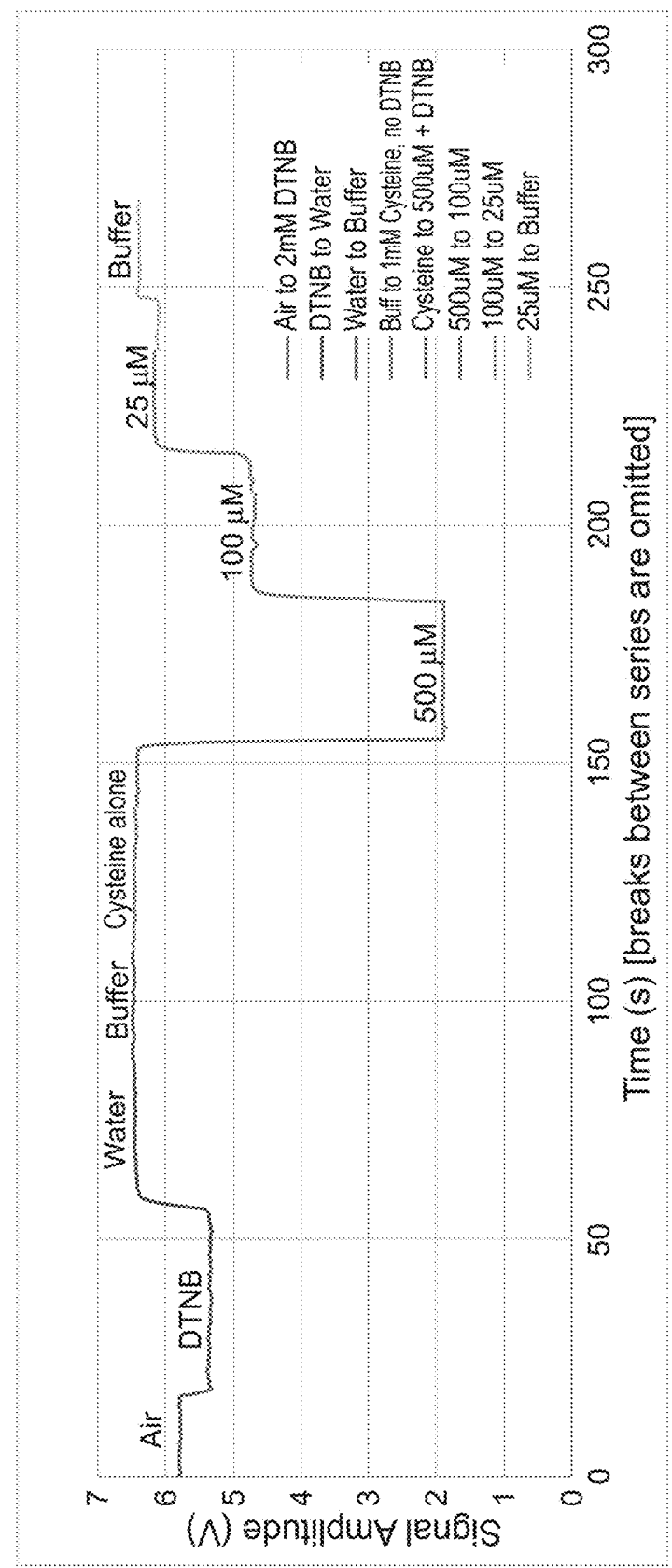
FIG. 9 depicts, in accordance with various embodiments of the present invention, calibration runs through the cysteine detection cartridge assembly.

As shown in FIG. 9, a calibration run was performed, by flowing the following solutions sequentially through the cysteine detection cartridge assembly and recording the detector voltage: air; 2 mM DTNB dissolved in water plus sodium acetate; water; Tris buffer 2.5 mM pH 5.5; cysteine 1000 µM not mixed with DTNB; cysteine reacted with an excess of DTNB with a final cysteine concentration of 500 µM, 100 µM and 25 µM; and Tris buffer 2.5 mM pH 5.5.

Figure 10:
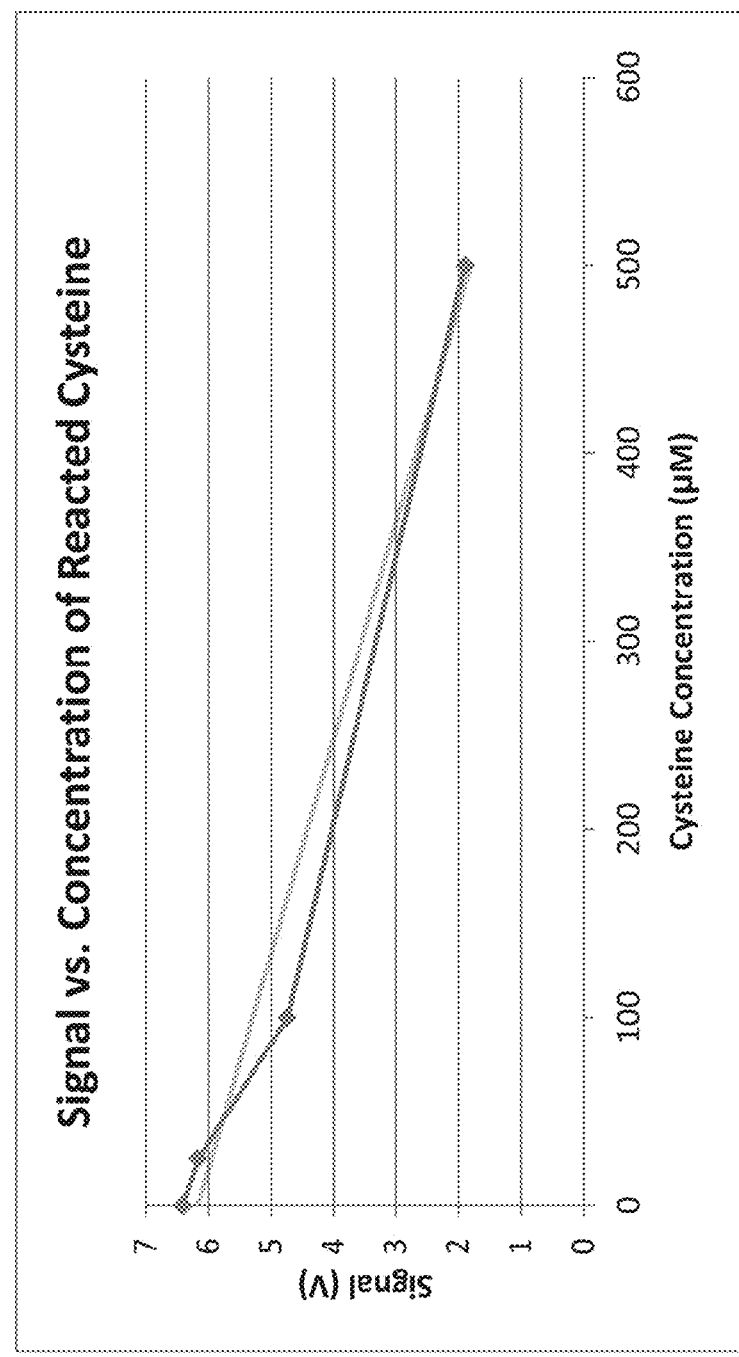
FIG. 10 depicts, in accordance with various embodiments of the present invention, a calibration plot between cysteine concentrations and signals in the cysteine detection cartridge assembly.
Figure 11:
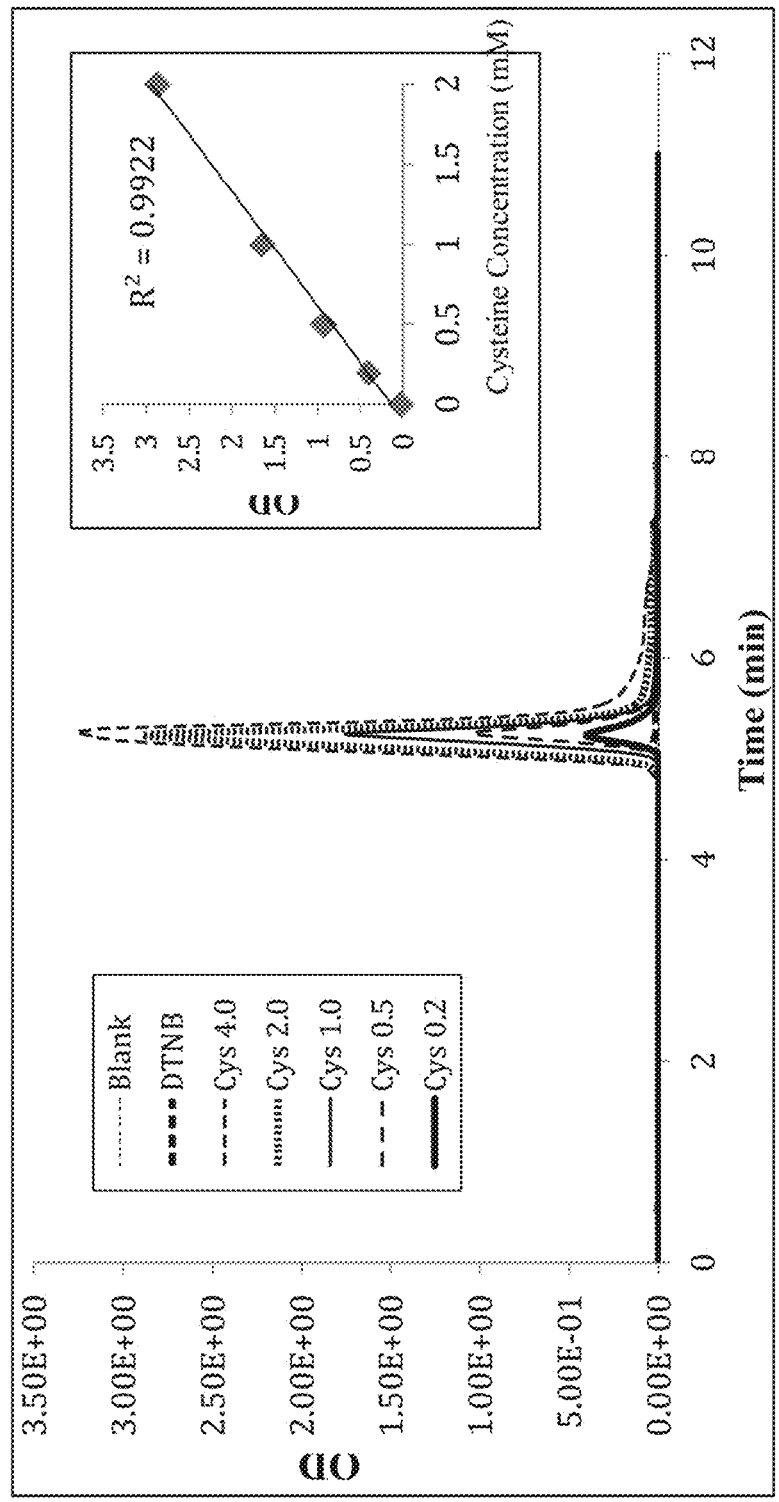
FIG. 11 depicts, in accordance with various embodiments of the present invention, cysteine detection using a method described herein as compared to a traditional method (e.g., HPLC). DTNB is retained for a period of time in C18 column using methanol-phosphate buffer mixture. Increase of DTNB absorption at 410 nm was observed in proportion with cysteine concentration in the solution. HPLC method is used to determine cysteine concentration in the buffer solution using DTNB, but the sensitivity of HPLC is not very prominent under 250 µM of cysteine concentration.

Before testing started, fresh mixtures of cysteine and DTNB were prepared. A calibration plot was obtained between cysteine concentrations and signals output from the cysteine detection cartridge assembly (FIG. 10).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

We claim:

1. A system, comprising:
   an enzyme reaction module comprising an enzyme reaction chamber comprising at least one inlet and at least one outlet, wherein the enzyme reaction chamber is configured to conduct a fluid flow from the at least one inlet, through the enzyme reaction chamber, to the at least one outlet;
   a sequestration-liberation module comprising a sequestration-liberation chamber comprising at least one second inlet and at least one second outlet and having gold particles located therein, wherein the sequestration-liberation chamber is configured to conduct a fluid flow from the at least one second inlet, through the sequestration-liberation chamber, to the at least one second outlet, and further comprising a set of electrodes configured to conduct an electric current through the gold particles; and
   a detection module comprising a detection channel comprising at least one third inlet and at least one third outlet, wherein the detection channel is configured to conduct a fluid flow from the at least one third inlet, through the detection channel, to the at least one third outlet, and a first aperture and a second aperture, wherein the detection channel is located between the first and second apertures, and wherein the first and second apertures are configured to conduct a light beam from the first aperture, across the detection channel, to the second aperture; and
   wherein the system is configured to conduct a fluid flow from the enzyme reaction module, through the sequestration-liberation module, to the detection module.

2. The system of claim 1, further comprising a biological sample obtained from a subject, cystathionine synthase, cystathionine lyase, wash or exchange buffer, and detection reagent.

3. The system of claim 1, wherein the enzyme reaction chamber is shaped as a column having a length of about 1-1000 mm and a diameter of about 0.1-100 mm.

4. The system of claim 2, wherein the cystathionine synthase and/or cystathionine lyase is immobilized on a solid support.

5. The system of claim 1, wherein the enzyme reaction module further comprises a filter located before the enzyme reaction chamber along a fluid flow pathway, and configured to filter a biological sample, enzyme, reagent, buffer, fluid flow, and/or reaction mixture.

6. The system of claim 1, wherein the sequestration-liberation chamber is shaped as a column having a length of about 1-1000 mm and/or a diameter of about 0.1-100 mm.

7. The system of claim 1, wherein the set of electrodes is configured to apply a voltage of about 1-10V.

8. The system of claim 1, further comprising a buffer cartridge configured to hold a wash or exchange buffer having a pH of about 8-14, and to supply the wash or exchange buffer to at least one inlet of the sequestration-liberation chamber.

9. The system of claim 1, wherein the detection channel has a width of about 0.1-1000 mm.

10. The system of claim 1, wherein the at least one third inlet of the detection channel is configured to receive a detection reagent.

11. The system of claim 1, wherein the detection module further comprises a third aperture and an optical filter located between the second and third apertures, wherein the second and third apertures are configured to conduct a light beam from the second aperture, across the optical filter which filters the light beam, to the third aperture.

12. The system of claim 11, wherein the detection module further comprises a light source configured to emit a light beam into the first aperture, and a photosensor configured to detect the light beam transmitted out of the third aperture, the photosensor configured to generate a current or voltage output from detected transmission light.

13. The system of claim 11, further comprising a spectrometer configured to emit a light beam into the first aperture and to detect transmission light intensity out of the third aperture.

14. A system, comprising:
   an enzyme reaction module comprising an enzyme reaction chamber comprising at least one inlet and at least one outlet, wherein the enzyme reaction chamber is configured to conduct a fluid flow from the at least one inlet, through the enzyme reaction chamber, to the at least one outlet;
   a sequestration-liberation module comprising a sequestration-liberation chamber comprising at least one second inlet and at least one second outlet, wherein the sequestration-liberation chamber is configured to conduct a fluid flow from the at least one second inlet, through the sequestration-liberation chamber, to the at least one second outlet, gold particles inside the sequestration-liberation chamber, and electrodes configured to conduct an electric current through the gold particles; and
   a detection module comprising a detection channel comprising at least one third inlet and at least one third outlet, wherein the detection channel is configured to conduct a fluid flow from the at least one third inlet, through the detection channel, to the at least one third outlet;
   a first aperture, a second aperture, a third aperture, and an optical filter, wherein the detection channel is located between the first aperture and the second aperture, wherein the optical filter is located between the second aperture and the third aperture, and wherein the three apertures and the optical filter are configured to conduct a light beam from the first aperture, across the detection channel, to the second aperture, across the optical filter, to the third aperture;
   a light source configured to emit a light beam into the first aperture; and
   a photosensor configured to detect the light beam transmitted out of the third aperture and to generate a current or voltage output from the detected transmission light; and
   wherein the system is configured to conduct a fluid flow from the enzyme reaction module, through the sequestration-liberation module, to the detection module.

15. The system of claim 14, further comprising a biological sample obtained from a subject, cystathionine synthase, cystathionine lyase, wash or exchange buffer, and detection reagent.

16. The system, comprising according to claim 14 wherein the light source is a spectrometer configured to emit a light beam into the first aperture and detect the transmission light intensity out of the third aperture.

17. A method, comprising:
   providing a system of claim 1;
   supplying a biological sample obtained from a subject, cystathionine synthase, cystathionine lyase, wash or exchange buffer, and detection reagent into the system;

operating the system to generate a current or voltage output; and using the generated current or voltage output to calculate a cysteine and/or methionine metabolite level in the biological sample.

18. The method of claim 17, further comprising diagnosing or prognosticating a cancer based on the detected cysteine and/or methionine metabolite level.

19. A method, comprising: providing a system of claim 14;

supplying a biological sample obtained from a subject, cystathionine synthase, cystathionine lyase, wash or exchange buffer, and detection reagent into the system; operating the system;

detecting a transmission light intensity out of the third aperture; and using the detected transmission light intensity to calculate a cysteine and/or methionine metabolite level in the biological sample.

20. The method of claim 19, further comprising diagnosing or prognosticating a cancer based on the detected cysteine and/or methionine metabolite level.

* * * * *

SEQUENCE LISTING

<160> NUMBER OF SEQ ID NOS: 14

<210> SEQ ID NO 1
<211> LENGTH: 305
<212> TYPE: PRT
<213> ORGANISM: Helicobacter pylori 908

<400> SEQUENCE: 1

Met Ile Leu Thr Ala Met Gln Asp Ala Ile Gly Arg Thr Pro Ile Phe
1               5                   10                  15

Lys Phe Thr Arg Lys Asp Tyr Pro Ile Pro Leu Lys Ser Ala Ile Tyr
            20                  25                  30

Ala Lys Leu Glu His Leu Asn Pro Gly Gly Ser Val Lys Asp Arg Leu
        35                  40                  45

Gly Gln Tyr Leu Ile Lys Glu Ala Phe Arg Thr His Lys Ile Thr Ser
    50                  55                  60

Thr Thr Thr Ile Ile Glu Pro Thr Ala Gly Asn Thr Gly Ile Ala Leu
65                  70                  75                  80

Ala Leu Val Ala Ile Lys His His Leu Lys Thr Ile Phe Val Val Pro
                85                  90                  95

Glu Lys Phe Ser Val Glu Lys Gln Gln Ile Met Arg Ala Leu Gly Ala
            100                 105                 110

Leu Val Ile Asn Thr Pro Thr Ser Glu Gly Ile Ser Gly Ala Ile Lys
        115                 120                 125

Lys Ser Lys Glu Leu Ala Glu Ser Ile Pro Asp Ser Tyr Leu Pro Leu
130                 135                 140

Gln Phe Glu Asn Pro Asp Asn Pro Ala Ala Tyr Tyr His Thr Leu Ala
145                 150                 155                 160

Pro Glu Ile Val Lys Glu Leu Gly Thr Asn Phe Thr Ser Phe Val Ala
                165                 170                 175

Gly Ile Gly Ser Gly Gly Thr Phe Ala Gly Thr Ala Lys Tyr Leu Lys
            180                 185                 190

Glu Arg Ile Pro Asn Ile Arg Leu Ile Gly Val Glu Pro Glu Gly Ser
        195                 200                 205

Ile Leu Asn Gly Gly Glu Pro Gly Pro His Glu Ile Glu Gly Ile Gly
    210                 215                 220

Val Glu Phe Ile Pro Pro Phe Phe Ala Asn Leu Asp Ile Asp Gly Phe
225                 230                 235                 240

Glu Thr Ile Ser Asp Glu Glu Gly Phe Ser Tyr Thr Arg Lys Leu Ala
            245                 250                 255

Lys Lys Asn Gly Leu Leu Val Gly Ser Ser Ser Gly Ala Ala Phe Ala
            260                 265                 270

Ala Ala Leu Lys Glu Val Gln Arg Leu Pro Glu Gly Ser Gln Val Leu
        275                 280                 285

Thr Ile Phe Pro Asp Met Ala Asp Arg Tyr Leu Ser Lys Gly Ile Tyr
    290                 295                 300

Ser
305

<210> SEQ ID NO 2
<211> LENGTH: 1215
<212> TYPE: DNA
<213> ORGANISM: Artificial Sequence
<220> FEATURE:
<223> OTHER INFORMATION: synthetic construct

<400> SEQUENCE: 2
atgaccccgg tgtctggcaa cctgaaagtc gaattttaca actccaatcc gtctgatacc      60
acgaatagca ttaacccgca gttcaaagtt acgaacaccg gcagctctgc gattgatctg     120
tcaaaactga cgctgcgtta ttactatacc gtcgatggtc agaaagacca aaccttttgg     180
tgcgaccatg cggccattat cggtagtaac ggctcctaca atggcattac gtctaatgtc     240
aaaggcacct tcgtgaaaat gagttcctca cgaacaatg gcgccggtgc aggcgctatg      300
atcctgaccg cgatgcagga tgccatcggc cgtacgccga tttttaaatt caccccgcaaa    360 gactacccga tcccgctgaa aagtgcaatt tatgctaaac tggaacatct gaatccgggc     420
ggcagcgtga agatcgtctg ggtcaatat ctgattaaag aagccttttcg cacgcacaaa     480 atcaccagca ccacgaccat tatcgaaccg acggcgggta ataccggtat cgcactggcc     540
ctggttgcca ttaaacatca cctgaaaacc atctttgtgg ttccggaaaa attctcagtc     600
gaaaaacagc aaatcatgcg tgcgctgggc gccctggtga tcaacacgcc gacctcagaa     660
ggtatctcgg cgcaattaa aaaatcgaaa gaactggctg aaagcattcc ggattcttac     720
ctgccgctgc aatttgaaaa cccggacaat ccggcagctt actatcatac cctggcaccg     780
gaaattgtga agaactggg cacgaatttt accagcttcg ttgctggtat cggctctggc     840
ggtacgttcg caggcaccgc taaatatctg aagaacgta ttccgaacat ccgcctgatt      900
ggcgtggaac cggaaggtag tattctgaat ggcggtgaac cgggtccgca cgaaatcgaa     960
ggtattggcg ttgaatttat cccgccgttt ttcgccaacc tggatattga cggctttgaa    1020
acgatttcag atgaagaagg tttctcgtat acccgcaaac tggcgaagaa aaacggtctg    1080
ctggttggca gcagcagcgg tgcagcattt gcagctgcgc tgaaagaagt tcagcgtctg    1140
ccggaaggca gccaagtcct gaccatttc cggatatgg cggaccgcta cctgagtaaa      1200
ggtatctatt cctaa                                                     1215

<210> SEQ ID NO 3
<211> LENGTH: 18
<212> TYPE: DNA
<213> ORGANISM: Artificial Sequence
<220> FEATURE:
<223> OTHER INFORMATION: synthetic construct

<400> SEQUENCE: 3
ggcgccggtg caggcgct                                                  18

<210> SEQ ID NO 4
<211> LENGTH: 279
<212> TYPE: DNA
<213> ORGANISM: Artificial Sequence
<220> FEATURE:
<223> OTHER INFORMATION: synthetic construct

<400> SEQUENCE: 4
atgaccccgg tgtctggcaa cctgaaagtc gaattttaca actccaatcc gtctgatacc     60
acgaatagca ttaacccgca gttcaaagtt acgaacaccg gcagctctgc gattgatctg    120
tcaaaactga cgctgcgtta ttactatacc gtcgatggtc agaaagacca aaccttttgg    180
tgcgaccatg cggccattat cggtagtaac ggctcctaca atggcattac gtctaatgtc    240
aaaggcacct tcgtgaaaat gagttcctca acgaacaat                           279

<210> SEQ ID NO 5
<211> LENGTH: 404
<212> TYPE: PRT
<213> ORGANISM: Artificial Sequence
<220> FEATURE:
<223> OTHER INFORMATION: synthetic consruct

<400> SEQUENCE: 5

Met Thr Pro Val Ser Gly Asn Leu Lys Val Glu Phe Tyr Asn Ser Asn
1               5                   10                  15

Pro Ser Asp Thr Thr Asn Ser Ile Asn Pro Gln Phe Lys Val Thr Asn
            20                  25                  30

Thr Gly Ser Ser Ala Ile Asp Leu Ser Lys Leu Thr Leu Arg Tyr Tyr
        35                  40                  45

Tyr Thr Val Asp Gly Gln Lys Asp Gln Thr Phe Trp Cys Asp His Ala
    50                  55                  60

Ala Ile Ile Gly Ser Asn Gly Ser Tyr Asn Gly Ile Thr Ser Asn Val
65                  70                  75                  80

Lys Gly Thr Phe Val Lys Met Ser Ser Ser Thr Asn Asn Gly Ala Gly
                85                  90                  95

Ala Gly Ala Met Ile Leu Thr Ala Met Gln Asp Ala Ile Gly Arg Thr
            100                 105                 110

Pro Ile Phe Lys Phe Thr Arg Lys Asp Tyr Pro Ile Pro Leu Lys Ser
        115                 120                 125

Ala Ile Tyr Ala Lys Leu Glu His Leu Asn Pro Gly Gly Ser Val Lys
    130                 135                 140

Asp Arg Leu Gly Gln Tyr Leu Ile Lys Glu Ala Phe Arg Thr His Lys
145                 150                 155                 160

Ile Thr Ser Thr Thr Thr Ile Ile Glu Pro Thr Ala Gly Asn Thr Gly
                165                 170                 175

Ile Ala Leu Ala Leu Val Ala Ile Lys His His Leu Lys Thr Ile Phe
            180                 185                 190

Val Val Pro Glu Lys Phe Ser Val Glu Lys Gln Gln Ile Met Arg Ala
        195                 200                 205

Leu Gly Ala Leu Val Ile Asn Thr Pro Thr Ser Glu Gly Ile Ser Gly
    210                 215                 220

Ala Ile Lys Lys Ser Lys Glu Leu Ala Glu Ser Ile Pro Asp Ser Tyr
225                 230                 235                 240

```
Leu Pro Leu Gln Phe Glu Asn Pro Asp Asn Pro Ala Ala Tyr Tyr His
                    245                 250                 255

Thr Leu Ala Pro Glu Ile Val Lys Glu Leu Gly Thr Asn Phe Thr Ser
            260                 265                 270

Phe Val Ala Gly Ile Gly Ser Gly Thr Phe Ala Gly Thr Ala Lys
        275                 280                 285

Tyr Leu Lys Glu Arg Ile Pro Asn Ile Arg Leu Ile Gly Val Glu Pro
    290                 295                 300

Glu Gly Ser Ile Leu Asn Gly Glu Pro Gly Pro His Glu Ile Glu
305                 310                 315                 320

Gly Ile Gly Val Glu Phe Ile Pro Pro Phe Ala Asn Leu Asp Ile
                325                 330                 335

Asp Gly Phe Glu Thr Ile Ser Asp Glu Glu Gly Phe Ser Tyr Thr Arg
            340                 345                 350

Lys Leu Ala Lys Lys Asn Gly Leu Leu Val Gly Ser Ser Gly Ala
        355                 360                 365

Ala Phe Ala Ala Ala Leu Lys Glu Val Gln Arg Leu Pro Glu Gly Ser
    370                 375                 380

Gln Val Leu Thr Ile Phe Pro Asp Met Ala Asp Arg Tyr Leu Ser Lys
385                 390                 395                 400

Gly Ile Tyr Ser

<210> SEQ ID NO 6
<211> LENGTH: 6
<212> TYPE: PRT
<213> ORGANISM: Artificial Sequence
<220> FEATURE:
<223> OTHER INFORMATION: synthetic construct

<400> SEQUENCE: 6

Gly Ala Gly Ala Gly Ala
1               5

<210> SEQ ID NO 7
<211> LENGTH: 93
<212> TYPE: PRT
<213> ORGANISM: Artificial Sequence
<220> FEATURE:
<223> OTHER INFORMATION: synthetic construct

<400> SEQUENCE: 7

Met Thr Pro Val Ser Gly Asn Leu Lys Val Glu Phe Tyr Asn Ser Asn
1               5                   10                  15

Pro Ser Asp Thr Thr Asn Ser Ile Asn Pro Gln Phe Lys Val Thr Asn
            20                  25                  30

Thr Gly Ser Ser Ala Ile Asp Leu Ser Lys Leu Thr Leu Arg Tyr Tyr
        35                  40                  45

Tyr Thr Val Asp Gly Gln Lys Asp Gln Thr Phe Trp Cys Asp His Ala
    50                  55                  60

Ala Ile Ile Gly Ser Asn Gly Ser Tyr Asn Gly Ile Thr Ser Asn Val
65                  70                  75                  80

Lys Gly Thr Phe Val Lys Met Ser Ser Ser Thr Asn Asn
                85                  90

<210> SEQ ID NO 8
<211> LENGTH: 378
<212> TYPE: PRT
<213> ORGANISM: Artificial Sequence
<220> FEATURE:
```

<223> OTHER INFORMATION: Helicobacter pylori 908

<400> SEQUENCE: 8

```
Met Gln Thr Lys Leu Ile His Gly Gly Ile Ser Glu Asp Ala Thr Thr
1               5                   10                  15

Gly Ala Val Ser Val Pro Ile Tyr Gln Ala Ser Thr Tyr Arg Gln Asp
            20                  25                  30

Ala Ile Gly Arg His Lys Gly Tyr Glu Tyr Ser Arg Ser Gly Asn Pro
        35                  40                  45

Thr Arg Phe Ala Leu Glu Glu Leu Ile Ala Asp Leu Glu Gly Gly Val
    50                  55                  60

Lys Gly Phe Ala Phe Ala Ser Gly Leu Ala Gly Ile His Ala Val Phe
65                  70                  75                  80

Ser Leu Leu Gln Ser Gly Asp His Val Leu Leu Gly Asp Asp Val Tyr
                85                  90                  95

Gly Gly Thr Phe Arg Leu Phe Asn Lys Val Leu Val Lys Asn Gly Leu
            100                 105                 110

Ser Cys Thr Ile Ile Asp Thr Ser Asp Ile Ser Gln Ile Lys Lys Ala
        115                 120                 125

Ile Lys Pro Asn Thr Lys Ala Leu Tyr Leu Glu Thr Pro Ser Asn Pro
    130                 135                 140

Leu Leu Lys Ile Thr Asp Leu Ala Gln Cys Ala Ser Val Ala Lys Asp
145                 150                 155                 160

His Gly Leu Leu Thr Ile Val Asp Asn Thr Phe Ala Thr Pro Tyr Cys
                165                 170                 175

Gln Asn Pro Leu Leu Leu Gly Ala Asp Ile Val Ala His Ser Gly Thr
            180                 185                 190

Lys Tyr Leu Gly Gly His Ser Asp Val Val Ala Gly Leu Val Thr Thr
        195                 200                 205

Asn Asn Glu Ala Leu Ala Gln Glu Ile Ala Phe Phe Gln Asn Ala Ile
    210                 215                 220

Gly Gly Val Leu Gly Pro Gln Asp Ser Trp Leu Leu Gln Arg Gly Ile
225                 230                 235                 240

Lys Thr Leu Gly Leu Arg Met Glu Ala His Gln Lys Asn Ala Leu Cys
                245                 250                 255

Val Ala Glu Phe Leu Glu Lys His Pro Lys Val Glu Arg Val Tyr Tyr
            260                 265                 270

Pro Gly Leu Pro Thr His Pro Asn His Glu Leu Ala Lys Ala Gln Met
        275                 280                 285

Arg Gly Phe Ser Gly Met Leu Ser Phe Thr Leu Lys Asn Asp Ser Glu
    290                 295                 300

Ala Ala Leu Phe Val Glu Ser Leu Lys Leu Phe Ile Leu Gly Glu Ser
305                 310                 315                 320

Leu Gly Gly Val Glu Ser Leu Val Gly Ile Pro Ala Leu Met Thr His
                325                 330                 335

Ala Cys Ile Pro Lys Glu Gln Arg Glu Ala Ala Gly Ile Arg Asp Gly
            340                 345                 350

Leu Val Arg Leu Ser Val Gly Ile Glu His Glu Gln Asp Leu Leu Glu
        355                 360                 365

Asp Leu Glu Gln Ala Phe Ala Lys Ile Ser
    370                 375
```

<210> SEQ ID NO 9
<211> LENGTH: 1434

<212> TYPE: DNA
<213> ORGANISM: Artificial Sequence
<220> FEATURE:
<223> OTHER INFORMATION: synthetic construct

<400> SEQUENCE: 9

```
atgacgccgg tgtctggcaa tctgaaagtg gaattttaca acagcaaccc gagcgatacg      60
acgaatagca tcaacccgca gttcaaagtg accaacacgg gtagctctgc gattgatctg     120
tctaaactga ccctgcgtta ttactatacg gttgatggcc agaaagacca aacctttttgg    180
tgcgaccatg cggccattat cggttctaac ggcagttata atggtatcac cagcaatgtg     240
aaaggcacgt tcgttaaaat gagttcctca accaacaatg gcgcaggtgc tggcgcgatg     300
cagacgaaac tgattcatgg cggtatcagc gaagatgcaa ccacgggtgc agtctcggtg     360
ccgatttacc aggccagcac ctatcgtcaa gacgcaatcg gtcgccacaa aggctacgaa     420
tattcgcgta gcggtaaccc gacgcgcttt gcactggaag aactgattgc ggatctggaa     480
ggcggtgtga aggctttgc cttcgcatca ggtctggcag catccatgc tgttttctcg       540
ctgctgcaaa gcggtgacca cgtcctgctg ggcgatgacg tgtacggcgg caccttttcgc   600
ctgttcaaca aagttctggt caaaaatggt ctgagttgta ccattatcga tacgtccgac     660
atttcacaga tcaaaaaagc gattaaaccg aacaccaaag ccctgtatct ggaaacgccg     720
tcgaatccgc tgctgaaaat taccgatctg gcccagtgcg caagcgttgc taaagatcat     780
ggcctgctga cgatcgtgga taacaccttt gcgacgccgt actgtcaaaa tccgctgctg     840
ctgggtgcgg atattgtcgc ccattccggc accaaatatc tgggcggtca ctcagacgtg     900
gttgccggtc tggttaccac gaacaatgaa gctctggcgc aggaaattgc gttttttccaa    960
aacgcaatcg gcgtgtgct gggtccgcag gatagctggc tgctgcaacg tggtatcaaa     1020
accctgggcc tgcgcatgga agcgcatcag aaaaatgcac tgtgcgttgc tgaatttctg    1080
gaaaaacacc cgaaagtgga acgtgtttac tatccgggtc tgccgaccca tccgaaccac   1140
gaactggcca aagcacaaat gcgcggtttt tctggcatgc tgagtttcac gctgaaaaat    1200
gattctgaag cagctctgtt tgtggaaagt ctgaaactgt tcattctggg tgaatccctg    1260
ggcggtgtcg aatcactggt gggcattccg gcactgatga cccatgcttg tatcccgaaa    1320
gaacagcgtg aagcggccgg tattcgtgat ggcctggttc gcctgtctgt cggcatcgaa    1380
cacgaacagg atctgctgga agacctggaa caggcgtttg cgaaaattag ttaa           1434
```

<210> SEQ ID NO 10
<211> LENGTH: 18
<212> TYPE: DNA
<213> ORGANISM: Artificial Sequence
<220> FEATURE:
<223> OTHER INFORMATION: synthetic construct

<400> SEQUENCE: 10

```
ggcgcaggtg ctggcgcg                                                    18
```

<210> SEQ ID NO 11
<211> LENGTH: 279
<212> TYPE: DNA
<213> ORGANISM: Artificial Sequence
<220> FEATURE:
<223> OTHER INFORMATION: synthetic construct

<400> SEQUENCE: 11

```
atgacgccgg tgtctggcaa tctgaaagtg gaattttaca acagcaaccc gagcgatacg      60
```

```
acgaatagca tcaacccgca gttcaaagtg accaacacgg gtagctctgc gattgatctg    120
tctaaactga ccctgcgtta ttactatacg gttgatggcc agaaagacca aacctttttgg   180 tgcgaccatg cggccattat cggttctaac ggcagttata atggtatcac cagcaatgtg    240
aaaggcacgt tcgttaaaat gagttcctca accaacaat                           279
```

<210> SEQ ID NO 12
<211> LENGTH: 477
<212> TYPE: PRT
<213> ORGANISM: Artificial Sequence
<220> FEATURE:
<223> OTHER INFORMATION: synthetic construct

<400> SEQUENCE: 12

```
Met Val Ser Tyr Lys Cys Gly Val Lys Asp Gly Thr Lys Asn Thr Ile
1               5                   10                  15

Arg Ala Thr Ile Asn Ile Lys Asn Thr Gly Thr Thr Pro Val Asn Leu
            20                  25                  30

Ser Asp Ile Lys Val Arg Tyr Trp Phe Thr Ser Asp Gly Glu Asn Asn
        35                  40                  45

Phe Val Cys Asp Tyr Ala Ala Phe Gly Thr Asp Lys Val Lys Lys Lys
    50                  55                  60

Ile Glu Asn Ser Val Pro Gly Ala Asp Thr Tyr Cys Glu Ile Ser Val
65                  70                  75                  80

Lys Gly Thr Phe Val Lys Met Ser Ser Thr Asn Asn Gly Ala Gly
                85                  90                  95

Ala Gly Ala Met Gln Thr Lys Leu Ile His Gly Gly Ile Ser Glu Asp
            100                 105                 110

Ala Thr Thr Gly Ala Val Ser Val Pro Ile Tyr Gln Ala Ser Thr Tyr
        115                 120                 125

Arg Gln Asp Ala Ile Gly Arg His Lys Gly Tyr Glu Tyr Ser Arg Ser
    130                 135                 140

Gly Asn Pro Thr Arg Phe Ala Leu Glu Glu Leu Ile Ala Asp Leu Glu
145                 150                 155                 160

Gly Gly Val Lys Gly Phe Ala Phe Ala Ser Gly Leu Ala Gly Ile His
                165                 170                 175

Ala Val Phe Ser Leu Leu Gln Ser Gly Asp His Val Leu Leu Gly Asp
            180                 185                 190

Asp Val Tyr Gly Gly Thr Phe Arg Leu Phe Asn Lys Val Leu Val Lys
        195                 200                 205

Asn Gly Leu Ser Cys Thr Ile Ile Asp Thr Ser Asp Ile Ser Gln Ile
    210                 215                 220

Lys Lys Ala Ile Lys Pro Asn Thr Lys Ala Leu Tyr Leu Glu Thr Pro
225                 230                 235                 240

Ser Asn Pro Leu Leu Lys Ile Thr Asp Leu Ala Gln Cys Ala Ser Val
                245                 250                 255

Ala Lys Asp His Gly Leu Leu Thr Ile Val Asp Asn Thr Phe Ala Thr
            260                 265                 270

Pro Tyr Cys Gln Asn Pro Leu Leu Leu Gly Ala Asp Ile Val Ala His
        275                 280                 285

Ser Gly Thr Lys Tyr Leu Gly Gly His Ser Asp Val Val Ala Gly Leu
    290                 295                 300

Val Thr Thr Asn Asn Glu Ala Leu Ala Gln Glu Ile Ala Phe Phe Gln
305                 310                 315                 320

Asn Ala Ile Gly Gly Val Leu Gly Pro Gln Asp Ser Trp Leu Leu Gln
```

```
                    325                 330                 335

Arg Gly Ile Lys Thr Leu Gly Leu Arg Met Glu Ala His Gln Lys Asn
                340                 345                 350

Ala Leu Cys Val Ala Glu Phe Leu Glu Lys His Pro Lys Val Glu Arg
            355                 360                 365

Val Tyr Tyr Pro Gly Leu Pro Thr His Pro Asn His Glu Leu Ala Lys
        370                 375                 380

Ala Gln Met Arg Gly Phe Ser Gly Met Leu Ser Phe Thr Leu Lys Asn
385                 390                 395                 400

Asp Ser Glu Ala Ala Leu Phe Val Glu Ser Leu Lys Leu Phe Ile Leu
                405                 410                 415

Gly Glu Ser Leu Gly Gly Val Glu Ser Leu Val Gly Ile Pro Ala Leu
            420                 425                 430

Met Thr His Ala Cys Ile Pro Lys Glu Gln Arg Glu Ala Ala Gly Ile
        435                 440                 445

Arg Asp Gly Leu Val Arg Leu Ser Val Gly Ile Glu His Glu Gln Asp
    450                 455                 460

Leu Leu Glu Asp Leu Glu Gln Ala Phe Ala Lys Ile Ser
465                 470                 475

<210> SEQ ID NO 13
<211> LENGTH: 6
<212> TYPE: PRT
<213> ORGANISM: Artificial Sequence
<220> FEATURE:
<223> OTHER INFORMATION: synthetic construct

<400> SEQUENCE: 13

Gly Ala Gly Ala Gly Ala
1               5

<210> SEQ ID NO 14
<211> LENGTH: 93
<212> TYPE: PRT
<213> ORGANISM: Artificial Sequence
<220> FEATURE:
<223> OTHER INFORMATION: synthetic construct

<400> SEQUENCE: 14

Met Val Ser Tyr Lys Cys Gly Val Lys Asp Gly Thr Lys Asn Thr Ile
1               5                   10                  15

Arg Ala Thr Ile Asn Ile Lys Asn Thr Gly Thr Thr Pro Val Asn Leu
                20                  25                  30

Ser Asp Ile Lys Val Arg Tyr Trp Phe Thr Ser Asp Gly Glu Asn Asn
            35                  40                  45

Phe Val Cys Asp Tyr Ala Ala Phe Gly Thr Asp Lys Val Lys Lys Lys
        50                  55                  60

Ile Glu Asn Ser Val Pro Gly Ala Asp Thr Tyr Cys Glu Ile Ser Val
65                  70                  75                  80

Lys Gly Thr Phe Val Lys Met Ser Ser Ser Thr Asn Asn
                85                  90
```